United States Patent
Eckenberg et al.

(10) Patent No.: US 6,194,424 B1
(45) Date of Patent: Feb. 27, 2001

(54) ARYLACETAMIDES AND THEIR USE AS MEDICAMENTS

(75) Inventors: Peter Eckenberg, Erkrath; Ulrich Müller, Wuppertal; Rudi Grützmann, Solingen; Hilmar Bischoff, Wuppertal; Dirk Denzer, Wuppertal; Ulrich Nielsch, Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/833,828

(22) Filed: Apr. 10, 1997

(30) Foreign Application Priority Data

Apr. 17, 1996 (DE) ................................................ 196 15 119

(51) Int. Cl.$^7$ ....................... A61K 31/437; C07D 471/06
(52) U.S. Cl. ................................................ 514/292; 546/87
(58) Field of Search ................................. 546/87; 514/292

(56) References Cited

U.S. PATENT DOCUMENTS

| | | |
|---|---|---|
| 4,906,654 | 3/1990 | Gillard et al. . |
| 5,420,149 | 5/1995 | Müller et al. . |
| 5,521,206 | 5/1996 | Müller et al. . |
| 5,527,809 | 6/1996 | Muller-Gliemann et al. . |
| 5,576,342 | 11/1996 | Müller et al. . |
| 5,684,014 * | 11/1997 | Muller et al. ........................ 514/292 |

FOREIGN PATENT DOCUMENTS

| | | |
|---|---|---|
| 234708 | 9/1987 | (EP) . |
| 513533 | 11/1992 | (EP) . |
| 705831 | 4/1996 | (EP) . |
| 753517 | 1/1997 | (EP) . |

* cited by examiner

*Primary Examiner*—Patricia L. Morris
(74) *Attorney, Agent, or Firm*—Norris McLaughlin & Marcus

(57) ABSTRACT

The new arylacetamides are obtained by first converting appropriately substituted arylacetic acids into the acetyl chlorides and then converting these into the amides using the appropriate amines. The new arylacetamides can be used as active compounds in medicaments, in particular in antiatherosclerotic medicaments.

6 Claims, No Drawings

ARYLACETAMIDES AND THEIR USE AS MEDICAMENTS

The present invention relates to new arylacetamides, processes for their preparation and their use as medicaments, in particular as antiatherosclerotic medicaments.

It is known that increased blood levels of triglycerides (hypertriglyceridaemia) and cholesterol (hypercholesterolaemia) are associated with the genesis of atherosclerotic vascular wall changes and coronary heart diseases.

A distinctly increased risk of the development of coronary heart diseases is moreover present if these two risk factors occur in combination, which in turn is accompanied by an overproduction of apolipoprotein B-100. There is therefore still a great need to make available effective medicaments for the control of atherosclerosis and of coronary heart diseases.

The present invention relates to new arylacetamides of the general formula (I)

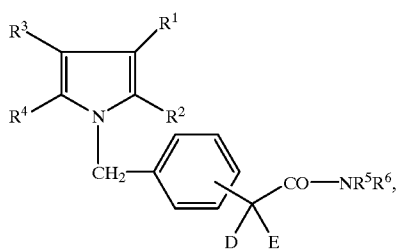

(I)

in which
R$^1$ and R$^2$, including the double bond connecting them, together form a phenyl

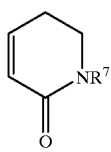

in which
R$^7$ denotes hydrogen or straight-chain or branched alkyl having up to 4 carbon atoms,
R$^3$ and R$^4$, including the double bond connecting them, together form a phenyl ring or a 4- to 8-membered cycloalkene or oxocycloalkene ring,
where all ring systems mentioned under R$^1$/R$^2$ and R$^3$/R$^4$ are optionally substituted up to 3 times in an identical or different manner by halogen, trifluoromethyl, carboxyl, hydroxyl, by straight- chain or branched alkoxy or alkoxycarbonyl each having up to 6 carbon atoms or by straight-chain or branched alkyl having up to 6 carbon atoms, which for its part can be substituted by hydroxyl or by straight-chain or branched alkoxy having up to 4 carbon atoms,
D and E are identical or different and represent hydrogen, cycloalkyl having 3 to 8 carbon atoms or straight-chain or branched alkyl having up to 10 carbon atoms, which is optionally substituted by cycloalkyl having 3 to 6 carbon atoms, or represent phenyl which is optionally substituted by halogen or trifluoromethyl,
or
D and E together, including the CH group, form a 4- to 8-membered carbocyclic system,
R$^5$ represents hydrogen, straight-chain or branched alkyl having up to 12 carbon atoms or cycloalkyl having 3 to 8 carbon atoms,
R$^6$ represents cycloalkyl having 3 to 8 carbon atoms or phenyl, or represents straight- chain or branched alkyl having up to 9 carbon atoms, which is optionally substituted by hydroxyl, naphthyl, trifluoromethyl or by a radical of the formula

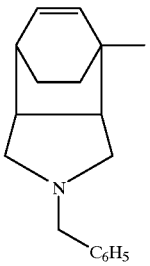

in which
a denotes a number 1 or 2
or
R$^6$ represents a radical of the formula —(CH$_2$)$_n$—R$^8$,
in which
n denotes a number 2, 3, 4 or 5,
R$^8$ denotes naphthyl or phenyl, each of which is optionally substituted by carboxyl, trifluoromethyl, halogen, hydroxyl, trifluoromethoxy or by straight-chain or branched alkyl, acyl, alkoxy or alkoxycarbonyl each having up to 6 carbon atoms,
or
represents a radical of the formula

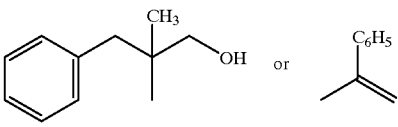

R$^5$ and R$^6$, together with the nitrogen atom, form a heterocyclic radical of the formula —(CH$_2$)$_2$—O—(CH$_2$)$_2$, —CH$_2$—(CH$_2$)$_p$—CH$_2$—,

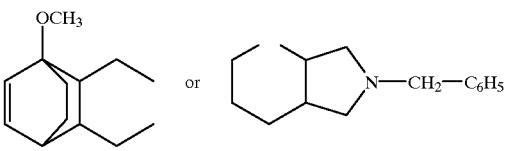

in which
p denotes a number 2, 3, 4, 5, 6, 7, 8 or 9,
if appropriate in an isomeric form, and their salts.

The new acrylacetamides according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Those particularly preferred are, for example, sodium, potassium, magnesium or calcium salts, as well as ammonium salts which are derived from ammonia, or organic amines, such as, for example, ethylamine, di- or triethylamine, di- or triethanolamine, dicyclohexylamine, dimethylaminoethanol, arginine, lysine, ethylenediamine or 2-phenylethylamine.

The cycloalkene radical ($R^3/R^4$), including the double bond of the parent structure, in the context of the invention in general represents a 4- to 8-membered, preferably 5- to 8-membered, hydrocarbon radical such as, for example, a cyclobutene, cyclopentene, cyclohexene, cycloheptene or cyclooctene radical. The cyclopentene, cyclohexene, cyclooctene and cycloheptene radicals are preferred.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. These mixtures of the enantiomers and diastereomers can be separated into the stereoisomerically uniform constituents in a known manner.

Preferred compounds of the general formula (I) are those in which $R^1$ and $R^2$, including the double bond connecting them, together form a phenyl or pyridyl ring or a ring of the formula

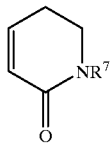

in which $R^7$ denotes hydrogen or straight-chain or branched alkyl having up to 3 carbon atoms, $R^3$ and $R^4$, including the double bond connecting them, together form a phenyl ring or a cyclopentene, cyclohexene, cycloheptene, cyclooctene, oxocyclopentene, oxocyclohexene, oxocycloheptene or oxocyclooctene radical, where all ring systems mentioned under $R^1/R^2$ and $R^3/R^4$ are optionally substituted up to 2 times in an identical or different manner by fluorine, chlorine, bromine, trifluoromethyl, carboxyl, hydroxyl, by straight-chain or branched alkoxy or alkoxycarbonyl each having up to 4 carbon atoms or by straight-chain or branched alkyl having up to 4 carbon atoms, which for its part can be substituted by hydroxyl or by straight-chain or branched alkoxy having up to 3 carbon atoms, D and E are identical or different and represent hydrogen, cyclopropyl, cyclobutyl, cyclopentyl, cyclohexyl, cycloheptyl, cyclooctyl or straight-chain or branched alkyl having up to 8 carbon atoms, which is optionally substituted by cyclopropyl, cyclopentyl or cyclohexyl, or represent phenyl which is optionally substituted by fluorine, chlorine or bromine, or D and E together, including the CH group, form a cyclobutyl, cyclopentyl, cyclohexyl, cycloheptyl or cyclooctyl ring, $R^5$ represents hydrogen, straight-chain or branched alkyl having up to 10 carbon atoms, cyclopropyl, cyclobutyl, cyclopentyl, cyclohexyl, cycloheptyl or cyclooctyl, $R^6$ represents cyclopropyl, cyclobutyl, cyclopentyl, cyclohexyl, cycloheptyl, cyclooctyl or phenyl, or represents straight-chain or branched alkyl having up to 7 carbon atoms, which is optionally substituted by hydroxyl, naphthyl, trifluoromethyl or by a radical of the formula

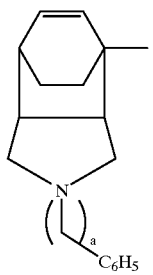

in which a denotes a number 1 or 2 or $R^6$ represents a radical of the formula $-(CH_2)_n-R^8$, in which n denotes a number 2, 3 or 4, $R^8$ denotes naphthyl or phenyl, each of which is optionally substituted by trifluoromethyl, fluorine, chlorine, bromine, hydroxyl, trifluoromethoxy or by straight-chain or branched alkyl, alkoxy or alkoxycarbonyl each having up to 5 carbon atoms, or represents a radical of the formula

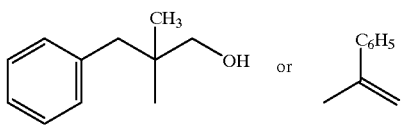

or $R^5$ and $R^6$, together with the nitrogen atom, form a heterocyclic radical of the formula $-(CH_2)_2-O-(CH_2)_2$, $-CH_2-(CH_2)_p-CH_2-$,

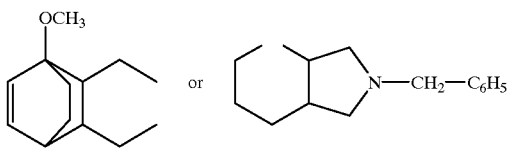

in which p denotes a number 2, 3, 4, 5, 6, 7 or 8, if appropriate in an isomeric form, and their salts.

Particularly preferred compounds of the general formula (I) are those in which

R¹ and R², including the double bond connecting them, together form a phenyl or pyridyl ring or a ring of the formula

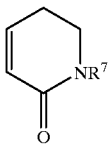

in which
R⁷ denotes hydrogen or methyl,
R³ and R⁴, including the double bond connecting them, together form a phenyl ring or a cyclopentene, cyclohexene, cycloheptene, cyclooctene, oxocyclopentene, oxocyclohexene, oxocycloheptene or oxocyclooctene radical,
where all ring systems mentioned under R¹/R² and R³/R⁴ are optionally substituted up to 2 times in an identical or different manner by fluorine, chlorine, bromine, trifluoromethyl, carboxyl, hydroxyl, by straight-chain or branched alkoxy or alkoxycarbonyl each having up to 3 carbon atoms or by straight-chain or branched alkyl having up to 3 carbon atoms, which for its part can be substituted by hydroxyl, methoxy or ethoxy,
D and E are identical or different and represent hydrogen, cyclopropyl, cyclobutyl, cyclopentyl, cyclohexyl, cycloheptyl, cyclooctyl or straight-chain or branched alkyl having up to 6 carbon atoms, which is optionally substituted by cyclopentyl or cyclohexyl, or represent phenyl which is optionally substituted by fluorine, chlorine or bromine,
or
D and E together, including the CH group, form a cyclopentyl, cyclohexyl or cycloheptyl ring,
R⁵ represents hydrogen, straight-chain or branched alkyl having up to 8 carbon atoms, cyclopentyl, cyclohexyl or cycloheptyl,
R⁶ represents cyclopentyl, cyclooctyl or phenyl, or represents straight-chain or branched alkyl having up to 6 carbon atoms, which is optionally substituted by hydroxyl, naphthyl, trifluoromethyl or by a radical of the formula

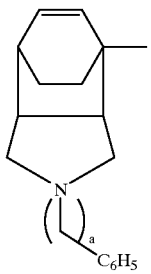

in which
a denotes a number 1 or 2
or
R⁶ represents a radical of the formula —(CH₂)ₙ—R⁸,
in which
n denotes a number 2 or 3,
R⁸ denotes naphthyl or phenyl, each of which is optionally substituted by trifluoromethyl, fluorine, chlorine, hydroxyl, trifluoromethoxy or by straight-chain or branched alkyl, alkoxy or alkoxycarbonyl each having up to 3 carbon atoms, or
represents a radical of the formula

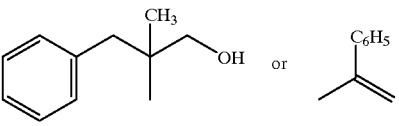

or
R⁵ and R⁶, together with the nitrogen atom, form a heterocyclic radical of the formula —(CH₂)₂—O—(CH₂)₂, —CH₂—(CH₂)ₚ—CH₂—,

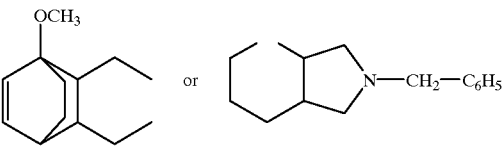

in which
p denotes a number 2, 3, 4, 5, 6 or 7,
if appropriate in an isomeric form, and their salts.
A process was additionally found, characterized in that starting from the (racemic or enantiomerically pure) carboxylic acids of the general formula (II)

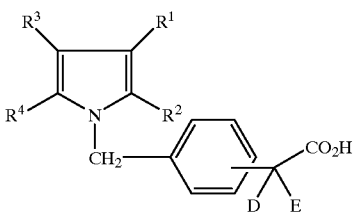

(II)

in which
D, E, R¹, R², R³ and R⁴ have the meaning indicated,
the corresponding (racemic or enantiomerically pure) acid chlorides of the general formula (III)

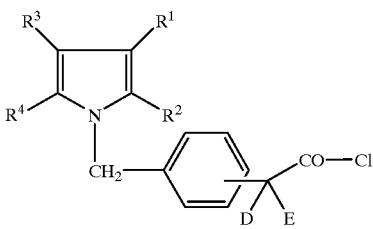

(III)

in which
D, E, R¹, R², R³ and R⁴ have the meaning indicated,
are first prepared
and finally reacted with amines of the general formula (IV)

HNR⁵R⁶ (IV)

in which
R⁵ and R⁶ have the meaning indicated,
in inert solvents, if appropriate in the presence of bases and/or auxiliaries.

The process according to the invention can be illustrated by way of example by the following equation:

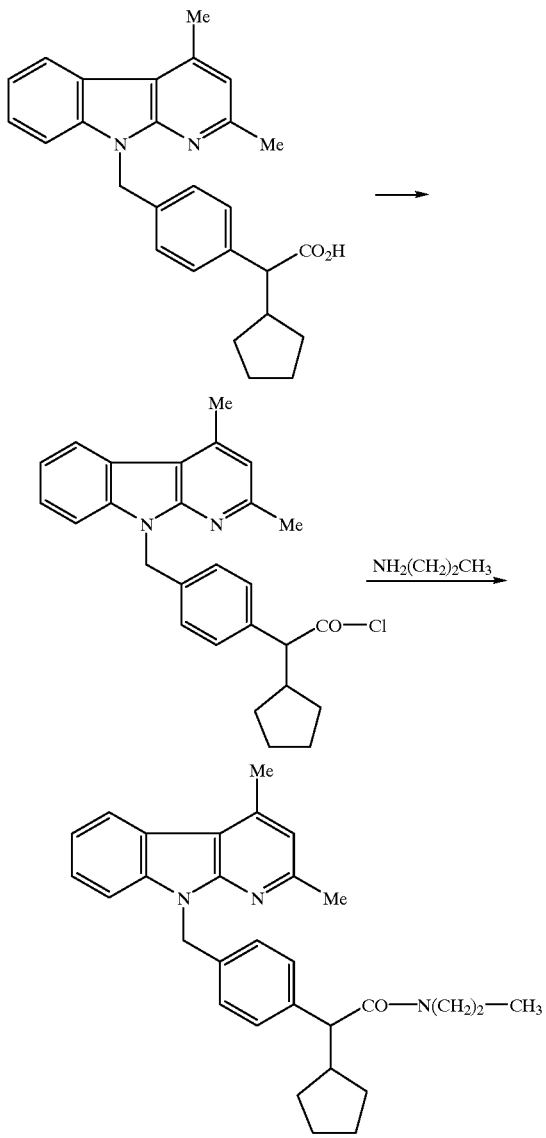

Suitable solvents here are inert organic solvents which do not change under the reaction conditions. These include ethers, such as diethyl ether or tetrahydrofuran, halo geno-hydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane, or petroleum fractions, nitromethane, ditnethylformamide, acetonitrile or hexamethylphosphoramide. It is also possible to employ mixtures of the solvents. Dichloromethane, tetrahydrofiran and dimethylformamide are particularly preferred.

Bases which can be employed for the process according to the invention are in general organic amines (trialkyl ($C_1$–$C_6$)amines) such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium and their hydrides such as sodium hydride. Pyridine and triethylamine are preferred.

The base is employed in an amount from 1 mol to 5 mol, preferably from 1 mol to 3 mol, relative to 1 mol of the compound of the general formula (III).

The reaction is in general carried out in a temperature range from 0° C. to 150° C., preferably from 0° C. to +25° C.

The reaction can be carried out at normal, elevated or reduced pressure (e.g. 0.5 to 5 bar). In general it is carried out at normal pressure.

The variation of functional groups such as, for example, hydrolysis, esterification and reduction, as well as isomer separation and salt formation is carried out according to customary methods.

The racemic carboxylic acids of the general formula (II) are new and can be prepared by a process in which first, by reaction of compounds of the general formula (V)

T-C

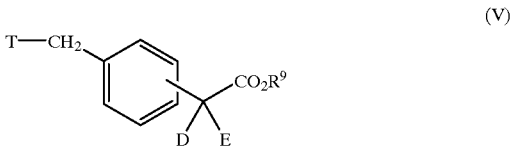

(V)

in which

D and E have the meaning indicated,

T represents a typical leaving group such as, for example, chlorine, bromine, iodine, tosylate or mesylate, preferably bromine, and $R^9$ represents ($C_1$–$C_4$)-alkyl, with compounds of the general formula (VI)

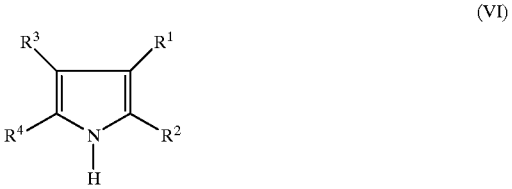

(VI)

in which $R^1$, $R^2$, $R^3$ and $R^4$ have the meaning indicated, the compounds of the general formula (VII)

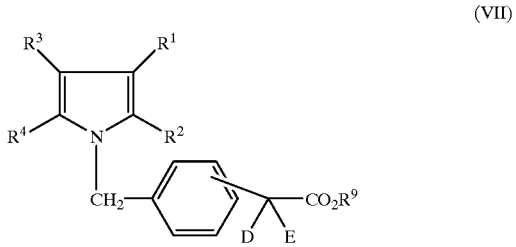

(VII)

in which

D, E, $R^1$, $R^2$, $R^3$, $R^4$ and $R^9$ have the meaning indicated, are prepared in inert solvents, if appropriate in the presence of bases and then the esters are hydrolysed according to customary methods.

The enantiomerically pure acids, i.e. compounds of the formula (II) in which D and E must be different, are moreover obtained by a process in which, starting first from the D- or L-menthyl esters of the general formula (VIII)

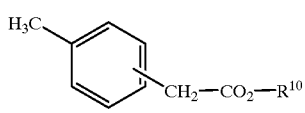
(VIII)

in which
$R^{10}$ represents D- or L-menthyl,
by reaction with compounds of the general formulae (IXa) and (IXb)

D-Z      (IXa)

E-Z      (IXb)

in which
D and E are different and otherwise have the meaning indicated,
and
Z represents halogen, preferably bromine,
the enantiomerically pure menthyl esters of the general formulae (Xa) and (Xb)

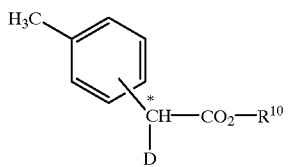
(Xa)

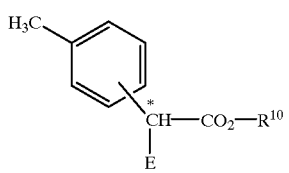
(Xb)

in which
D, E and $R^{10}$ have the meaning indicated,
are prepared,
these are converted in a next step by halogenation into the compounds of the general formulae (XIa) and (XIb)

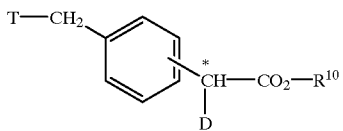
(XIa)

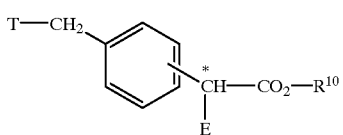
(XIb)

in which
D, E, T and $R^{10}$ have the meaning indicated,
from which then, by reaction with the compounds of the general formula (V), the enantiomerically pure compounds of the general formulae (XIIa) and (XIIb)

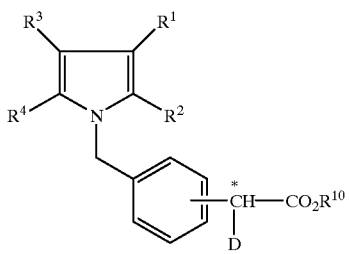
(XIIa)

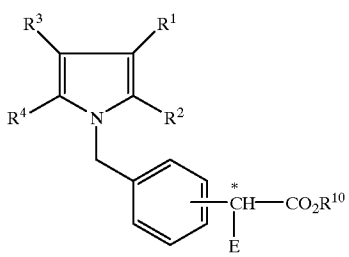
(XIIb)

in which
D, E, $R^1, R^2, R^3, R^4$ and $R^{10}$ have the meaning indicated,
are prepared,
and these are then converted by hydrolysis into the enantiomerically pure acids of the general formula (II).

Additionally, the enantiomerically pure acids of the formula (II) can be prepared by a process in which first racemic carboxylic acids of the general formula (XIII)

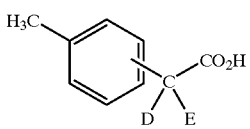
(XIII)

in which
D and E have the meaning indicated above,
are converted by reaction with (R)- or (S)-phenylethylamine in inert solvents and subsequent crystallization of the phenethylammonium salts and subsequent hydrolysis of the salts into the enantiomerically pure compounds of the general formula (XIVa,b)

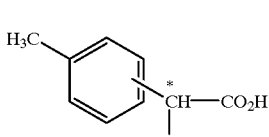
(XIVa)

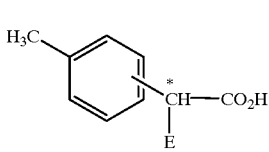
(XIVb)

in which
D and E have the meaning indicated above,
in a further step with isobutene, in inert solvents and in the presence of acids, the enantiomerically pure esters of the general formula (XVa,b)

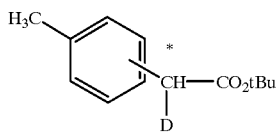
(XVa)

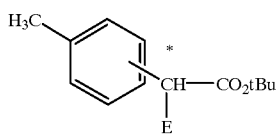
(XVb)

in which
D and E have the meaning indicated above,
are prepared,
converted as described above by halogenation into the enantiomerically pure compounds of the general formula (XVIa,b)

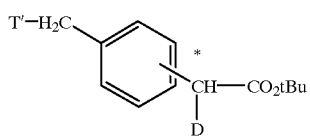
(XVIa)

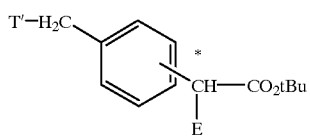
(XVIb)

in which
D and E have the meaning indicated above,
and
T' has the meaning of T indicated above and is identical to or different from this,
and converted by reaction with the compounds of the general formula (VI) into the enantiomerically pure esters of the general formula (XVIIa,b)

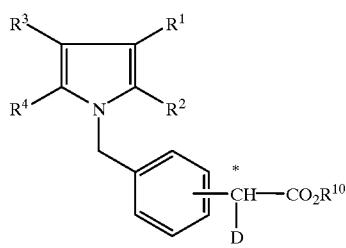
(XIIa)

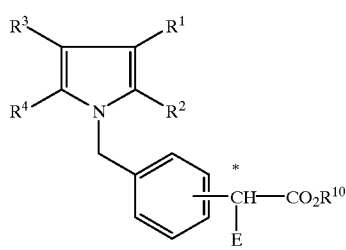
(XIIb)

in which

D, E, $R^1$, $R^2$, $R^3$ and $R^4$ have the meaning indicated above,
and in the last steps, as described above, corresponding enantiomerically pure acids and their derivatives are prepared.

Suitable solvents for the processes are customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or petroleum . fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide, toluene and tetrahydrofuran are preferred.

Bases which can be employed for the processes according to the invention are in general inorganic or organic bases. These preferably include alkali metal hydroxides such as, for example, sodium hydroxide or potassium hydroxide, alkaline earth metal hydroxides such as, for example, barium hydroxide, alkali metal carbonates and hydrogen carbonates such as sodium carbonate, sodium hydrogen carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines, such as triethylamine, or heterocycles such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as bases alkali metals such as sodium or their hydrides such as sodium hydride. Sodium hydrogen carbonate, potassium carbonate and potassium tert-butoxide, DBU or DABCO are preferred.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned.

If appropriate, the hydrolysis can also be carried out using acids such as, for example, trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at elevated pressure or at reduced pressure (e.g. from 0. 5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

The hydrolysis of tert-butyl esters is in general carried out using acids such as, for example, hydrochloric acid or trifluoroacetic acid, in the presence of one of the solvents indicated above and/or water or mixtures thereof, preferably using dioxane or tetrahydrofuran.

The preparation of the compounds of the general formulae (Xa) and (Xb) is preferably carried out in dimethylformamide and potassium tert-butoxide in a temperature range from −10° C. to +10° C.

The halogenation of the compounds of the general formulae (XIa) and (XIb) is carried out in chlorobenzene using 1,3-dibromo-5,5-dimethylhydantoin in the presence of azobisisobutyronitrile in a temperature range from 0° C. to 110° C.

The reaction to give the compounds of the general formulae (XIIa) and (XIIb) is carried out under a protective gas atmosphere in dimethylformamide and potassium tert-butoxide in a temperature range from 0° C. to 30° C.

The hydrolysis of the compounds of the general formulae (XIIa) an& (XIIb) can be carried out as described above, the system HBr/formic acid being particularly preferred. The hydrolysis is carried out in a temperature range from 20° C. to 100° C.

In the first step, the reaction to give the compounds of the general formulae (XIIIa) and (XIIb) is preferably carried out in tetrahydrofuran and triethylamine and, in the second step, in the system water/hydrochloric acid. The reaction is carried out in a temperature range from 30° C. to 70° C.

The acid employed for the preparation of the compounds of the general formulae (XVIa) and (XVIb) according to the invention is particularly preferably concentrated sulphuric acid. The preparation is carried out using methylene chloride.

In a further working-up step, potassium carbonate is employed as the base. The reaction is carried out in a temperature range from 0° C. to +20° C., particularly preferably at 10° C.

The halogenation of the compounds of the general formulae (XVIa) and (XVIb) is carried out using N-bromosuccinimide in carbon tetrachloride in the presence of azobisisobutyronitrile.

In general, the base is employed in an amount from 0.05 mol to 10 mol, preferably from 1 mol to 2 mol, in each case relative to 1 mol of the compounds of the general formulae (V), (IXa), (IXb), (XIIa), (XIIb), (XIIa) and (XIIIb).

The processes according to the invention are in general carried out at normal pressure. However, it is also possible to carry out the process at elevated pressure or at reduced pressure (e.g. in a range from 0.5 to 5 bar).

The compounds of the general formula (III) are new and can be prepared as described above.

The compounds of the general formulae (IV), (IXa) and (IXb) are known or can be prepared in analogy to known methods.

The compounds of the general formula (VI) are known in some cases or are new and can then be prepared, however, in analogy to published methods.

The compounds of the general formula (VIII) are new as a species and are prepared from the corresponding acid.

With the exception of D/E=CH-isopropyl, the enantiomerically pure compounds of the general formulae (Xa) and (Xb) are new and can be prepared as described above.

The compounds of the general formulae (XIa), (XIb), (XIIa), (XIIb) are new and can be prepared as described above.

The compounds of the general formula (IV) are known per se.

The compounds of the general formulae (XIVa) and (XIVb) are known in some cases or can be prepared by customary methods.

The enantiomerically pure compounds of the general formulae (XVIa), (XVIb), (XVIIa) and (XVIIb) are new and can be prepared as described above.

The compounds of the general formula (I) according to the invention have an unforeseeable spectrum of pharmacological action.

They can be used as active compounds in medicaments for the reduction of changes to vascular walls and for the treatment of coronary heart diseases, cardiac insufficiency, brain function disorders, ischaemic brain disorders, apoplexy, circulatory disorders, microcirculation disorders and thromboses.

Furthermore, the proliferation of smooth muscle cells plays a decisive part in the occlusion of vessels. The compounds according to the invention are suitable for inhibiting this proliferation and thus preventing atherosclerotic processes.

The compounds according to the invention are distinguished by a lowering of the ApoB-100-associated lipoproteins (VLDL and its degradation products such as, for example, LDL), of ApoB- 100, of triglycerides and of cholesterol. They thus have useful pharmacological properties which are superior in comparison with those of the prior art.

Surprisingly, the action of the compounds according to the invention consists first in a decrease or complete inhibition of the formation and/or the release of ApoB-100-associated lipoproteins from liver cells, which results in a lowering of the VLDL plasma level. This lowering of VLDL must be accompanied by a lowering of the plasma levels of ApoB-100, LDL, triglycerides and of cholesterol; several of the abovementioned risk factors which are involved in vascular wall changes are thus simultaneously lowered.

The compounds according to the invention can therefore be employed for the prevention and treatment of atherosclerosis, of obesity, pancreatitis and of constipation.

1. Inhibition of the release of ApoB-100-associated lipoproteins

The test for detection of the inhibition of the release of ApoB-100-associated lipoproteins from liver cells was carried out in vitro using cultured liver cells, preferably using cells of the human line HepG2. These cells are cultured under standard conditions in medium for the culture of eucaryotic cells, preferably in RPMI 1640 using 10% foetal calf serum. HepG2 cells synthesize and secrete into the culture supernatant ApoB-100-associated lipoprotein particles, which in principle are of similar construction to the VLDL or LDL particles which are to be, found in the plasma.

These particles can be detected using an immunoassay for human LDL. This immunoassay is carried out using antibodies which have been induced under standard conditions in the rabbit to human LDL. The anti-LDL antibodies (rabbit anti-LDL-Ab) were purified by affinity chromatography on an immunosorbent using human LDL. These purified rabbit anti-LDL-Ab are adsorbed onto the surface of plastic. Expediently, this adsorption takes place onto the plastic surface of microtitre plates having 96 depressions, preferably onto MaxiSorp plates. If ApoB-100-associated particles are present in the supernatant of Hep-G2 cells, these can bind to the insolubilized rabbit anti-LDL-Ab, and an immune complex is formed which is bound to the plastic surface. Unbound proteins are removed by washing. The immune complex on the plastic surface is detected using monoclonal antibodies which have been induced against human LDL and purified according to standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific light absorption at 450 nm is determined, which is a measure of the amount of ApoB-100-associated particles which have been secreted into the culture supernatant by the HepG2 cells.

Surprisingly, the compounds according to the invention inhibit the release of ApoB-100-associated particles. The $IC_{50}$ value indicates at which substance concentration the light absorption is inhibited by 50% in comparison with the control (solvent control without substance).

| Ex. No. | Apo B $IC_{50}$ [nM] |
|---|---|
| 2 | 8.2 |
| 20 | 12.5 |

2. Determination of the VLDL secretion in vivo in the hamster

The effect of the test substances on VLDL secretion in vivo is investigated in the hamster. To do this, golden hamsters are anaesthetized with Ketavet (83 mg/kg s.c.) and Nembutal (50 mg/kg i.p.) after premedication with atropine (83 mg/kg s.c.). When the animals have become reflex-free, the jugular vein is exposed and cannulated. 0.25 ml/kg of a 20% strength solution of Triton WR-1339 in physiological saline solution is then administered. This detergent inhibits the lipoprotein lipase and thus leads to a rise in the triglyceride level as a result of a lack of catabolism of secreted VLDL particles. This triglyceride rise can be used as a measure of the VLDL secretion rate. Blood is taken from the animals before and one and two hours after administration of the detergent by puncture of the retroorbital venous plexus. The blood is incubated for two hours at room temperature, then overnight at 4° C., in order to end coagulation completely. It is then centrifuged at 10,000 g for 5 minutes. In the serum thus obtained, the triglyceride concentration is determined with the aid of a modified commercially available enzyme test (Merckotest™ triglyceride No. 14354). 100 µl of serum are mixed with 100 µl of test reagent in 96-hole plates and the mixture is incubated at room temperature for 10 minutes. The optical density is then determined at a wavelength of 492 nm in an automatic plate reader (SLT spectra). Serum samples having too high a triglyceride concentration are diluted with physiological saline solution. The triglyceride concentration contained in the samples is determined with the aid of a standard curve measured in parallel. In this model, test substances are either administered intravenously immediately before administration of the detergent or orally or subcutaneously before initiation of anaesthesia.

3. Inhibition of the intestinal triglycende absorption in vivo (rats)

The substances which are to be investigated for their triglyceride absorption-inhibiting action in vivo are administered orally to male Wistar rats having a body weight of between 170 and 230 g. For this purpose, the animals are divided into groups of 6 animals 18 hours before substance administration and the feed is then withdrawn from them. Drinking water is available to the animals ad libitum. The animals of the control groups receive an aqueous tragacanth suspension or a tragacanth suspension which contains olive oil. The tragacanth-olive oil suspension is prepared using an Ultra-Turrax The substances to be investigated are likewise suspended in a corresponding tragacanth-olive oil suspension using the Ultra-Turrax, directly before substance administration.

Blood is taken from each rat by puncture of the retroorbital venous plexus before stomach tube application to determine the basal serum triglyceride content. The itragacanth suspension, the tragacanth- olive oil suspensions without substance (control animals), or the substances suspended in an appropriate tragacanth-olive oil suspension are then administered to the fasting animals using a stomach tube. Further taking of blood to determine the postprandial serum triglyceride rise as a rule takes place 1, 2 and 3 hours after stomach tube application.

The blood samples are centrifuged and, after recovering the serum, the triglycerides are determined photometrically using an EPOS analyser 5060 (EppendorfGeratebau, Netheler & Hinz GmbH, Hamburg). The determination of the triglycerides is carried out completely enzymatically using a commercially available UV test.

The postprandial serum triglyceride rise is determined by subtraction of the triglyceride preliminary value of each animal from its corresponding postprandial triglyceride concentrations (1, 2 and 3 hours after administration).

The differences (in mmol/l) at each time (1, 2 and 3 hours) are meaned in the groups, and the average values of the serum triglyceride rise (ΔTG) of the substance-treated animals are compared with the animals which only received the tragacanth-oil suspension.

The serum triglyceride course of the control animals which only received tragacanth is also calculated. The substance effect at each time (1, 2 or 3 hours) is determined as follows and indicated in Δ% of the oil-loaded control.

$$\Delta\% \text{ triglyceride rise} = \frac{\Delta TG_{substance} - \Delta TG_{tragacanth\ control}}{\Delta TG_{oil\ loading} - \Delta TG_{tragacanth\ control}} \times 100$$

Effect of 1, 3 or 10 mg of test substance/kg of body weight p.o. on the triglyceride rise (Δ%) 2 h after a triglyceride loading in the serum of fasting rats. The serum triglyceride rise of fat-loaded control animals relative to the serum triglyceride level of tragacanth control animals corresponds to 100%. n=6 animals per group.

| | Serum triglyceride rise in % (2 h pp) |
|---|---|
| Triglyceride loading | 100 |
| Tragacanth control | 0 |

Statistical analysis is carried out using Student's t-test after prior checking of the variances for homogeneity.

Substances which at one time statistically significantly ($p<0.05$) decrease by at least 30% the postprandial serum triglyceride rise, compared with the untreated control group, are regarded as pharmacologically active.

4. Inhibition of VLDL secretion in vivo (rat)

The action of the test substances on VLDL secretion is also investigated in the rat. To do this, Triton WR-1339 (2.5 mg/kg), dissolved in physiological saline solution, is administered intravenously into the tail vein of rats of 500 g body weight. Triton WR-1339 inhibits lipoprotein lipase and thus leads by inhibition of VLDL catabolism to a rise in the triglyceride and cholesterol level. These rises can be used as a measure of the VLDL secretion rate.

Before and two hours after administration of the detergent, blood is taken from the animals by puncture of the retroorbital venous plexus. The blood is incubated at room temperature for 1 h for coagulation and the serum is recovered by centrifugation at 10 000 g for 20 s. The triglycerides are then determined photometrically at a wavelength of 540 nm by means of a commercially available coupled enzyme test (Sigma Diagnostics®, No. 339). Measurement is carried out with the aid of a likewise coupled enzyme test (Boehringer Mannheim®, No. 1442350) at a wavelength of 546 nm. Samples having triglyceride or cholesterol concentrations which exceed the measuring range of the methods are diluted with physiological saline solution. The determination of the respective serum concentrations is carried out with the aid of standard series measured in parallel. Test substances are administered orally, intravenously or subcutaneously immediately after the Triton injection.

The invention additionally relates to the combination of new arylacetamides of the general formula (I) with a glucosidase and/or amylase inhibitor for the treatment of familial hyperlipidaemias, of obesity (adiposity) and of diabetes mellitus. G lucosidase and/or amylase inhibitors in the context of the invention are, for example, acarbose, adiposine, voglibose, miglitol, emiglitate, MDL-25637, camiglibose (MDL-73945), tendamistate, AI-3688, trestatin, pradimicin-Q and salbostatin.

The combination of acarbose, miglitol, emiglitate or voglibose with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound here should in each case be present in a concentration of approximately 0.5 to 90% by weight of the total mixture, i.e. in amounts which are adequate in order to achieve the dosage range indicated.

The formulations are prepared, for example, by extending the active compounds with solvents and/or excipients, if appropriate using emulsifiers and/ or dispersants, it being possible, for example, if water is used as a diluent optionally to use organic solvents as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous in the case of intravenous administration to administer amounts from approximately 0.001 to 1 mg/kg, preferably approximately 0.01 to 0.5 mg/kg, of body weight to achieve effective results, and in the case of oral administration the dose is approximately 0.01 to 20 mg/kg, preferably 0.1 to 10 mg/kg, of body weight.

In spite of this, if appropriate it may be necessary to deviate from the amounts mentioned, namely depending on the body weight or on the type of administration route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual doses over the course of the day.

| Abbreviations used: | |
|---|---|
| Ac | = acetyl |
| Bn | = benzyl |
| Bz | = benzoyl |
| iBu | = isobutyl |
| nBu | = normal butyl |
| sBu | = secondary butyl |
| tBu | = tertiary butyl |
| DDQ | = 2,3-dichloro-5,6-dicyano-1,4-benzoquinone |
| cDec | = cyclodecyl |
| DMF | = N,N-dimethylformamide |
| DMSO | = dimethyl sulphoxide |
| cDodec | = cyclododecyl |
| Et | = ethyl |
| cHept | = cycloheptyl |
| cHex | = cyclohexyl |
| HOBT | = 1-hydroxy-1H-benzotriazole |
| Me | = methyl |
| Mes | = mesyl |
| cNon | = cyclononyl |
| cOct | = cyclooctyl |
| cPent | = cyclopentyl |
| nPent | = normal pentyl |
| Ph | = phenyl |
| cPr | = cyclopropyl |
| nPr | = normal propyl |
| iPr | = isopropyl |
| THF | = tetrahydrofuran |
| TMS | = tetramethylsilane |
| pTol | = paratolyl |
| pTos | = paratosyl |
| cUndec | = cycloundecyl |

| Solvent | Symbol |
|---|---|
| Dichloromethane : methanol = 20:1 | A |
| Dichloromethane : methanol = 50:1 | B |
| Dichloromethane : ethanol = 20:1 | C |
| Dichloromethane : ethanol = 50:1 | D |
| Petroleum ether : ethyl acetate = 1:1 | E |
| Dichloromethane : methanol : acetic acid = 90:10:2 | F |
| Petroleum ether : ethyl acetate = 2:1 | G |
| Petroleum ether : ethyl acetate = 10:1 | H |
| Toluene | I |
| Toluene : ethyl acetate = 1:1 | K |
| Petroleum ether : ethyl acetate = 5:1 | L |
| Dichloromethane | M |
| Petroleum ether : ethyl acetate = 20:1 | N |
| Dichloromethane : methanol = 10:1 | O |
| Cyclohexane : ethyl acetate = 1:1 | P |
| Toluene : ethyl acetate = 9:1 | Q |
| Toluene : ethyl acetate = 8:1 | R |
| Petroleum ether : ethyl actae = 1:2 | S |
| Dichloromethane : ethanol = 5:1 | T |
| Dichloromethane : ethanol = 10:1 | U |
| Petroleum ether : ethyl acetate = 9:1 | V |
| Dichloromethane : methanol = 19:1 | W |
| Petroleum ether : ethyl acetate = 4:1 | X |
| Dichloromethane : methanol = 100:1 | Y |
| Dichloromethane : methanol = 100:3 | Z |
| Petroleum ether : ethyl acetate = 6:1 | XA |

Preparation procedure for the TLC eluent BABA:

87.9 ml of an aqueous 0.06667 molar potassium dihydrogen phosphate solution and 12.1 ml of an aqueous 0.06667 molar disodium hydrogen phosphate solution are mixed. 60 ml of the solution prepared in this way are shaken with 200 ml of n-butyl acetate, 36 ml of n-butanol and 100 ml of glacial acetic acid and the aqueous phase is removed. The organic phase is the eluent BABA.

Starting Compounds

EXAMPLE I

6-Chloro-2,4-lutidine

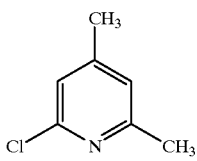

For the preparation of the title compound [U.S. Pat. No. 36 32 807], 600 g (4.91 mol) of 6-amino-2,4-lutidine are dissolved in 2 l of methanol and the solution is saturated at 0° C. with hydrogen chloride gas. 1.307 l (9.82 mol) of isopentyl nitrite are added dropwise at an internal temperature below 10° C. (about 2.5 h) and the mixture is then left for 15 h while warming to room temperature (about 25° C.). The solution is largely freed from the solvent in vacuo, mixed with 3 l of dichloromethane and 1.5 l of water and adjusted to pH=9.5 using concentrated aqueous ammonia solution with cooling (<20° C.). The organic phase removed is dried with sodium sulphate, first concentrated in vacuo on a rotary evaporator and then distilled through a Vigreux column:

Fraction 1) b.p.=47–49° C. (12 mm Hg), 603 g

Fraction 2) b.p.=82–85° C. (12 mm Hg), 612 g (about 88% crude)

$R_f$=0.39 (petroleum ether:ethyl acetate=10:1)

$^1$H-NMR (CDCl$_3$, 200 MHz, TMS): δ=2.28 (s, 3H), 2.47 (s, 3H), 6.88 (s, 1H), 6.96 (s, 1H) ppm.

The crude product, which may contain small amounts of 6-methoxy-2,4-lutidine, is reacted further without further purification.

EXAMPLE II

6-Hydrazino-2,4- lutidine (4,6- dimethyl-2-hydrazino-pyridine)

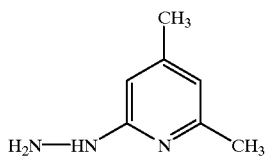

580 g (4.10 mol) of the compound from Example II are dissolved in 800 ml of diethylene glycol and stirred with 1050 ml of hydrazine hydrate for 48 h at a bath temperature of about 140° C. The cooled mixture is poured onto 4.5 l of ether and 4.5 l of water and the organic phase is extracted twice using 2.3 l of dichloromethane each time. The combined organic phases are dried using sodium sulphate and evaporated in vacuo. 784 g of solvent-containing crude product are obtained, which is reacted further without working up.

$R_f$=0.37 (dichloromethane:methanol=10:1)

$^1$H-NMR (d$_6$-DMSO, 250 MHz, TMS): δ=2.13 (s, 3H), 2.22 (s, 3H), 4.02 10 (s, 2H), 6.26 (s, 1H), 6.35 (s, 1H), 7.11 (s, 1H) ppm.

EXAMPLE III 2,4-Dimethyl-5,6,7,8-tetrahydro-α-carboline

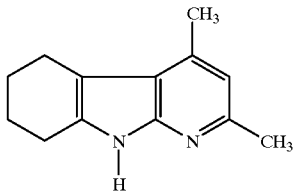

78 g (max. 0.49 mol) of crude compound from Example II are reacted at room temperature (about 25° C.) with 59 ml (0.56 mol) of cyclohexanone, whereupon the internal temperature rises. After 2 h, the starting material has disappeared (TLC checking, dichloromethane:methanol=10:1). The mixture is taken up in 40 ml of diethylene glycol and reacted under reflux, constituents which boil lower than the solvent (e.g. water of reaction and excess cyclohexanone) are removed in the course of this by distillation (water separator). After 3 h, the intermediate hydrazone has disappeared (TLC checking, petroleum ether:ethyl acetate=1:1); the reaction mixture is cooled to room temperature and stirred with acetone. The precipitate obtained is filtered off with suction, washed with acetone and dried in vacuo (34.4 g). The mother liquors largely freed from the solvent are in turn treated with acetone, a further 9.3 g of product being obtained. (total yield over 3 stages:43.7 g/0.22 mol/47%).

M.p.: 248° C. (uncorrected)

$R_f$=0.41 (dichloromethane:ethanol=20:1)

$^1$H-NMR (d$_6$-DMSO, 200 MHz, TMS): δ=1.78 (m, 4H), 2.40 (s, 3H), 2.48 (s, 3H), 2.64 (m, 2H), 2.82 (m, 2H), 6.57 (s, 1H), 10.84 (s, 1H) ppm.

The compounds of Table I are prepared analogously to the procedure of Example III:

TABLE I

| Ex. No. | Structure | $R_f$ (Solvent) | Starting material (Hydrazine *) |
|---|---|---|---|
| IV | (cyclopenta-fused pyrrolopyridine with 4-CH₃ and 2-CH₃) | 0.59 (A) | Ex. No. II |
| V | (cyclohepta-fused pyrrolopyridine with 4-CH₃ and 2-CH₃) | 0.36 (E) | Ex. No. II |
| VI | (cyclohexa-fused pyrrolopyridine with 4-CF₃ and 2-CH₃) | 0.45 (G) | |
| VII | (cyclohexa-fused pyrrolopyridine with 2-CH₃) | 0.46 (E) | |
| VIII | (cyclohexa-fused pyrrolopyridine with 4-CH₃ and 2-CH₃) | 0.06 (L) | |
| IX | (cyclopenta-fused pyrrolopyridine with 2-CH₃) | 0.41 (E) | |
| X | (cyclohepta-fused pyrrolopyridine with 2-CH₃) | 0.40 (E) | |
| XI | (cyclopenta-fused pyrrolopyridine, unsubstituted) | 0.59 (O) | |

TABLE I-continued

| Ex. No. | | $R_f$ (Solvent) | Starting material (Hydrazine *) |
|---|---|---|---|
| XII | (structure: cycloheptane fused indole-pyridine, NH) | 0.34 (E) | |
| XIII | (structure: cyclooctane fused indole-pyridine with 4-CH₃ and 2-CH₃, NH) | 0.42 (E) | |
| XIV | (structure: cyclopentane fused indole-pyridine with 4-CH₃ and 2-CH₃, NH) | 0.59 (G) | |
| XV | (structure: cycloheptane fused indole-pyridine with 4-CF₃ and 2-CH₃, NH) | 0.85 (G) | |

EXAMPLE XVI 2,4-Dimethyl-α-carboline

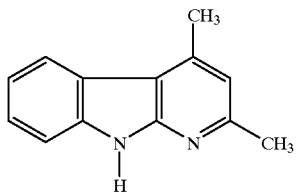

100 g (499 mmol) of the compound from Example III are reacted under reflux in 700 ml of diethylene glycol with 164 ml (1 mol) of diethyl fumarate on 52 g of palladium (5% on carbon). At the high internal temperature, a small amount of ethanol distils off (if appropriate use a water separator). After about 8 h the starting material has disappeared (TLC checking, petroleum ether:ethyl acetate=1:1, detection in the iodine chamber). The cooled mixture is treated with 3 l of acetone, boiled, and solid is filtered off hot with suction through a clarifying filter (Seitz) and washed with 1 l of hot acetone. On cooling, a precipitate is obtained which, after filtering off with suction, rinsing with cold acetone and drying in vacuo, yields 58.3 g of product. The mother liquor is largely freed from acetone in vacuo, the precipitae which is deposited being worked up as above (9.4 g). The filtrate is in turn freed from acetone; after addition of n-pentane product precipitates a further time (3.1 g/working-up see above); total yield: 72%.

M.p.: 220–221° C. (uncorrected)

$R_f$=0.47 (petroleum ether:ethyl acetate=1:1)

$^1$H-NMR (d$_6$-DMSO, 200 MHz, TMS): δ=2.54 (s, 3H), 2.75 (s, 3H), 6.89 (s, 1H), 7.20 (m, 1H), 7.40 (m, 1H), 7.48 (dd, 1H), 8.05 (dd, 1H), 11.61 (s, 1H) ppm.

EXAMPLE XVII tert-Butyl 2(R,S)-2-cyclopentyl-2-[4-(2,4-dimethyl-α-carbolin-9-yl)methyl]-phenyl-acetate

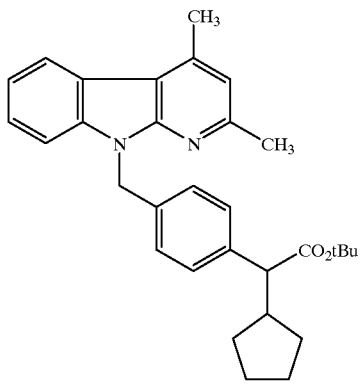

73.6 g (375 mmol) of the compound from Example XVI are reacted for 30 min at 25° C. in 700 ml of anhydrous N,N-dimnethylformamide with 42.13 g (375 mmol) of potassium tert-butoxide and then treated with 161.7 g (375 mmol) of the compound from Example XXVII, dissolved in 680 ml of anhydrous N,N-dimethylformamide. After 1 h, the reaction is complete (TLC checking, petroleum ether:ethyl acetate=10:1). For working up, 2 l of buffer solution (pH= 4/Merck) and 2 l of water are added, and the precipitate obtained is filtered off with suction, washed with water and rapidly filtered off with suction again. The moderately damp solid is then stirred successively with petroleum ether and methanol and filtered off with suction. Vacuum drying over phosphorus pentoxide yields 139.8 g (298 mol/790/) of product.

M.p.: 160–161° C. (uncorrected)

$R_f$=0.39 (petroleum ether:ethyl acetate=10:1)

$^1$H-NMR (CDCl$_3$, 250 MHz, TMS): δ=0.91 (m, 1H), 1.18–1.68 (m, 6H), 1.87 (m, 1H), 1.47 (s, 9H), 2.42 (m, 1H), 2.66 (s, 3H), 2.83 (s, 3H), 3.09 (d, 1H), 5.6 (s, 2H), 6.8 (s, 1H), 7.13–7.41 (m, 7H), 8.09 (d, 1H) ppm.

The compounds of Tables II and III are prepared analogously to the procedure of Example XVIII:

TABLE II

| Ex. No. | $R^{11}$ | D | $R_f$ (Solvent) |
|---|---|---|---|
| XVIII | 2,4-dimethyl-5,6,7,8-tetrahydro-α-carbolin-9-yl (N-CH₃) | cPent | 0.28 (H) |
| XIX | 2,4-dimethyl-α-carbolin-9-yl (N-CH₃) | cHept | 0.47 (H) |
| XX | 2,4-dimethyl-cyclopenta[b]pyrrolo-pyridinyl (N-CH₃) | cHept | 0.54 (L) |

TABLE II-continued

[Structure: 4-(R11-methyl)phenyl with CH(D)CO2tBu group, racemic]

| Ex. No. | R11 | D | R_f (Solvent) |
|---------|-----|---|---------------|
| XXI | 1,2-dimethyl-tetrahydro-pyrido[2,3-b]indole (6-membered carbocycle, N-Me) | cHept | 0.27 (H) |
| XXII | 1,2-dimethyl-cyclohepta-fused pyrido[2,3-b]indole (7-membered carbocycle, N-Me) | cPent | 0.59 (D) |
| XXIII | 1,2-dimethyl-cyclohepta-fused pyrido[2,3-b]indole (7-membered carbocycle, N-Me) | cHept | 0.29 (H) |
| XXIV | 4-CF3, 2-CH3 tetrahydro-pyrido[2,3-b]indole (6-membered carbocycle, N-Me) | cPent | 0.70 (M) |
| XXV | 4-CF3, 2-CH3 tetrahydro-pyrido[2,3-b]indole (6-membered carbocycle, N-Me) | cHept | 0.36 (H) |
| XXVI | 4-CH3 tetrahydro-pyrido[2,3-b]indole (6-membered carbocycle, N-Me, no 2-methyl) | cHept | 0.48 (L) |

TABLE II-continued

[Structure shown: racemic compound with R¹¹-CH₂- attached to para-position of benzene ring, with benzylic carbon bearing CO₂tBu and D groups]

| Ex. No. | R¹¹ | D | R_f (Solvent) |
|---------|-----|---|---------------|
| XXVII | 9-methyl-β-carboline (pyrido[3,4-b]indole, N-Me) | cPent | 0.49 (C) |
| XXVIII | 9-methyl-α-carboline (pyrido[2,3-b]indole, N-Me) | cPent | 0.51 (C) |
| XXIX | 9-methyl-β-carboline-3-carboxylic acid ethyl ester (CO₂C₂H₅ substituent) | cPent | 0.54 (C) |
| XXX | 1,3-dimethyl-9-methyl-6,7,8,9-tetrahydro-carbazole (CH₃ groups) | cPent | 0.37 (N) |
| XXXI | 1,3-dimethyl-9-methyl-6,7,8,9-tetrahydro-carbazole | cHept | 0.56 (H) |
| XXXII | 7-methoxy-1,9-dimethyl-β-carboline (H₃CO, CH₃ substituents) | cPent | 0.57 (C) |
| XXXIII | 2,4-dimethyl-9-methyl-tetrahydro-α-carboline | cHex | 0.35 (H) |

TABLE II-continued

[Structure: racemic compound with R11-CH2 group on benzene ring, with CH(D)(CO2tBu) substituent]

| Ex. No. | R11 | D | Rf (Solvent) |
|---------|-----|---|--------------|
| XXXIV | [4-methyl-2-methyl-9-methyl-pyrido[2,3-b]indole] | cHex | 0.57 (B) |
| XXXV | [9-methyl-2-methyl-1-oxo-2,3,4,9-tetrahydro-β-carboline] | cPent | M.p. = 189–190° C. |
| XXXVI | [4-methyl-2-methyl-9-methyl-pyrido[2,3-b]indole] | iBu | 0.49 (M) M.p.: 142° C. MS (CI/NH3): 457 (100%) |

TABLE III

| Ex. No. | R12 | D | Rf (Solvent) MS/M.p. |
|---------|-----|---|----------------------|
| XXVII | [4-methyl-2-methyl-9-methyl-pyrido[2,3-b]indole] | iPr | 0.39 (M) Fp: = 159° C. MS(CI/NH3): 401 (100%) |
| XXXVIII | [2-methyl-9-methyl-pyrido[2,3-b]indole] | cPent | 0.76 (B) |
| XXXIX | [4-methyl-2-methyl-9-methyl-tetrahydro-pyrido[2,3-b]indole] | cHept | 0.26 (H) |
| XL | [9-methyl-tetrahydro-pyrido[2,3-b]indole] | cHept | 0.64 (K) |
| XLI | [2-methyl-9-methyl-tetrahydro-pyrido[2,3-b]indole] | cHept | 0.29 (H) |

TABLE III-continued

| Ex. No. | R[12] | D | R_f (Solvent) MS/M.p. |
|---|---|---|---|
| XLII | (4-methyl, 2-methyl α-carboline) | | cHept 0.30 (H) |

EXAMPLE XLIII 2-(R,S)-2-Cyclopentyl-2-[4-(2,4-dimethyl-α-carbolin-9-yl)methyl]phenylacetic acid hydrochloride

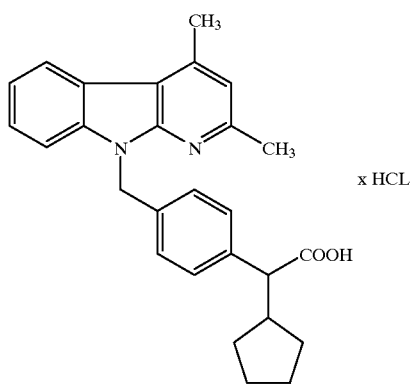

139.8 g (298 mmol) of the compound from Example XVII are dissolved in 1 l of 1,4-dioxane and stirred at 70° C. for 3 h with 240 ml of concentrated hydrochloric acid (37% strength). After reaction is complete (TLC checking; petroleum ether:ethyl acetate=10:1), the mixture is cooled to about 15° C. and then poured in portions onto 5 l of water. The pH is adjusted to 2.8 using 2 M aqueous sodium hydroxide solution, and the filtrate obtained is filtered off with suction through a filter paper and washed with water until the wash water has a pH of >4. The solid rapidly filtered off with suction is stirred with 1 l of petroleum ether (boiling range 60–80° C.), filtered off with suction again and dried in vacuo over phosphorus pentoxide.

Yield: 130.3 g (290 mmol/97%)

M.p.: 260–262° C. (uncorrected)

$R_f$=0.51 (dichloromethane:ethanol=20:1)

$^1$H-NMR (d$_6$-DMSO, 200 MHz, TMS): δ=0.88 (m, 1H), 1.09–1.67 (m, 6H), 1.79 (m, 1H), 2.38 (m, 1H), 2.68 (s, 3H), 2.84 (s, 3H), 3.16 (d, 1H), 4.7–5.9 (1H), 5.80 (s, 2H), 7.12–7.26 (m, 5H), 7.3 (m, 1H), 7.49 (m, 1H), 7.59 (d, 1H), 8.17 (d, 1H) ppm.

The compounds of Table IV are prepared analogously to the procedure of Example XLIII:

TABLE IV

| Ex. No. | R[13] | D | R_f (Solvent) |
|---|---|---|---|
| XLIV | (4-methyl, 2-methyl tetrahydro-α-carboline) | racemic | cPent 0.37 (A) |

TABLE IV-continued

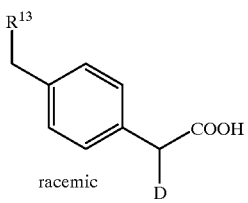

| Ex. No. | R[13] | D | R_f (Solvent) |
|---|---|---|---|
| XLV | 4-methyl-2-methyl-9-methyl-9H-pyrido[2,3-b]indole | cHept | 0.23 (G) |
| XLVI | 4-methyl-2-methyl-N-methyl cyclopenta-fused pyrrolopyridine | cHept | 0.30 (E) |
| XLVII | 4-methyl-2-methyl-N-methyl cyclohexa-fused pyrrolopyridine | cHept | 0.27 (D) |
| XLVIII | 4-methyl-2-methyl-N-methyl cyclohepta-fused pyrrolopyridine | cPent | 0.37 (C) |
| XLIX | 4-methyl-2-methyl-N-methyl cyclohepta-fused pyrrolopyridine | cHept | 0.15 (C) |
| L | 4-CF$_3$-2-methyl-N-H cyclohexa-fused pyrrolopyridine | cPent | 0.43 (A) |

TABLE IV-continued $$\text{R}^{13}\text{-CH}_2\text{-}\underset{\text{racemic}}{\text{C}_6\text{H}_4}\text{-CH(D)-COOH}$$

| Ex. No. | R[13] | D | R_f (Solvent) |
|---|---|---|---|
| LI | 4-CF₃-2-CH₃-6,7,8,9-tetrahydro-9-methyl-β-carbolin-3-yl (pyrido-indole with CF₃ and CH₃) | cHept | 0.27 (C) |
| LII | 4-CH₃-6,7,8,9-tetrahydro-9-methyl-β-carbolin-3-yl | cHept | 0.17 (E) |
| LIII | 9-methyl-9H-pyrido[3,4-b]indol-3-yl | cPent | 0.07 (C) |
| LIV | 9-methyl-9H-pyrido[2,3-b]indol-3-yl | cPent | 0.26 (C) |
| LV | 3-(ethoxycarbonyl)-9-methyl-9H-β-carbolin-1-yl | cPent | 0.39 (C) |
| LVI | 2,4-dimethyl-6,7,8,9-tetrahydro-9-methylcarbazol-3-yl | cPent | 0.46 (C) |
| LVII | 2,4-dimethyl-6,7,8,9-tetrahydro-9-methyl-β-carbolin-3-yl | cHept | 0.68 (E) |

TABLE IV-continued

Structure: racemic compound with R¹³-CH₂-phenyl-CH(D)-COOH

| Ex. No. | R¹³ | D | R_f (Solvent) |
|---------|-----|---|---------------|
| LVIII | 7-methoxy-1,9-dimethyl-β-carboline (H₃CO-, N-CH₃, CH₃ on pyridine ring) | cPent | 0.44 (C) |
| LIX | 2,4-dimethyl-tetrahydro-α-carboline | cHex | 0.44 (C) |
| LX | 2,4-dimethyl-9-methyl-β-carboline | cHex | 0.55 (C) |
| LXI | 2,9-dimethyl-1-oxo-tetrahydro-β-carboline | cPent | Fp. 204–205° C. |
| LXII | 2,4,9-trimethyl-β-carboline | iBu | 0.36 (A)<br>M.p: 156° C.<br>MS(FAB):<br>401(100%)<br>154 (90%) |

EXAMPLE LXIII

Methyl 4-tolyl-acetate

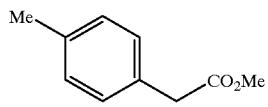

300 g (1.998 mol) of 4-tolyl-acetic acid are dissolved in 2.5 l of methanol, and the solution is stirred with 100 ml of concentrated sulphuric acid and refluxed for 2.5 hours. A total of 430 g (5.1 mol) of sodium hydrogen carbonate are gradually stirred into this mixture (evolution of carbon dioxide !), the methanol is largely evaporated in vacuo, the residue is partitioned between water and dichloromethane and the aqueous phase is reextracted with dichloromethane. The combined organic phases are dried using sodium sulphate and freed from the solvent in vacuo. The residue is distilled in a high vacuum.

Yield: 336 g

Boiling temperature=65° C. (0.5 mbar)

$R_f$=0.81 (toluene:ethyl acetate=2:1)

EXAMPLE LXIV

Ethyl 4-tolyl-acetate

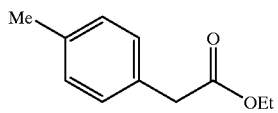

Starting from 4-tolyl-acetic acid, ethyl 4-tolyl-acetate is prepared analogously to the procedure of Example LXIII.
$R_f$=0.43 (N)

EXAMPLE LXV tert-Butyl 4-methylphenylacetate

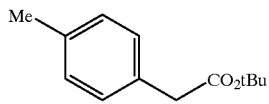

450 g (3 mol) of 4-methylphenylacetic acid, 1.13 l (12 mol) of tert-butanol and 90 g (0.74 mol) of dimethylaminopyridine are dissolved in 2 l of dichloromethane. After addition of 680 g (3.3 mol) of dicyclohexylcarbodiimide, dissolved in 400 ml of dichloromethane, the mixture is stirred at 25° C. for 20 h, the precipitated urea is filtered off with suction and washed with 200 ml of dichloromethane, and the organic phase is washed twice each with 500 ml of 2M hydrochloric acid and water. The organic phase is dried using sodium sulphate, concentrated and distilled.

Yield: 408 g (66%)

Boiling point: 73–78° C. (0.2 mm Hg)

EXAMPLE LXVI tert-Butyl 2-cyclopentyl-2-(4-methylphenyl)acetate

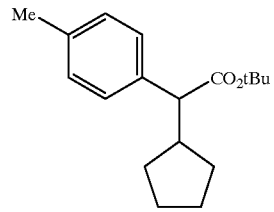

33.5 g (0.3 mol) of potassium tert-butoxide are initially introduced into 100 ml of DMF with exclusion of moisture at 0° C., and 51.6 g (0.25 mol) of the compound from Example LXV in 250 ml of DMF are added dropwise. The mixture is stirred at 0° C. for 30 min, 32.2 ml (0.3 mol) of cyclopentyl bromide in 150 ml of DMF are added dropwise at 5–15° C. and the mixture is stirred at 25° C. for 20 h. After concentrating, the residue is partitioned between water/diethyl ether, and the ether phase is dried over sodium sulphate and concentrated. Either: The product crystallizes.

Yield: 67 g (97.5%)

Melting point: 51–53° C.

TABLE III

The compounds of Table III are prepared analogously to the procedure of Example LXVI

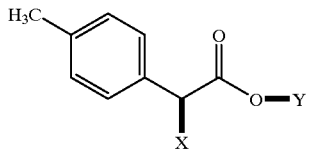

| Ex. No. | —X | —Y | a) M.p.(° C.) b) $R_f$ (Solvent) | Spektra | Starting material from Ex. No. |
|---|---|---|---|---|---|
| LXVII | —CH₃ = Me | —C(CH₃)₃ = tBu | b) 0.71 (I) | | LXV |
| LXVIII | —C₂H₅ = Et | tBu | b) 0.67 (I) | | LXV |
| LXIX | —CH₂CH₂CH₃ = nPr | tBu | b) 0.69 (I) | | LXV |
| LXX | —CH(CH₃)₂ = iPr | Me | b) 0.86 (toluene ethyl acetate = 9:1) | | LXIII |
| LXXI | —CH(CH₃)₂ = iPr | tBu | b) 0.76 (Q) | | LXV |
| LXXII | —CH₂CH₂CH₂CH₃ = nBu | tBu | b) 0.74 (I) | | LXV |
| LXXIII | —CH₂CH(CH₃)₂ = iBu | tBu | b) 0.70 (I) | | LXV |
| LXXIV | —CH₂CH₂CH₂CH₂CH₃ = nPent | tBu | b) 0.75 (V) | | LXV |
| LXXV | —CH₂CH₂—CH(CH₃)₂ = iPent | tBu | b) 0.54 (petroleum ether: ethyl acetate = 10:1) | | LXV |

TABLE III-continued

The compounds of Table III are prepared analogously to the procedure of Example LXVI

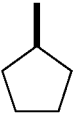

| Ex. No. | —X | —Y | a) M.p.(° C.)<br>b) $R_f$ (Solvent) | Spektra | Starting material from Ex. No. |
|---|---|---|---|---|---|
| LXXVI | —CH(CH$_2$CH$_3$)$_2$ | tBu | | MS: 276 (M$^+$, 4%) | LXV |
| LXXVII | —CH$_2$CH$_2$CH$_2$CH$_2$CH$_2$CH$_3$ = nHex | tBu | b) 0.75 (I) | | LXV |
| LXXVIII | —CH$_2$CH(CH$_2$CH$_3$)$_2$ | tBu | | MS: 290 (M$^+$, 1%) | LXV |
| LXXIX | 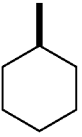 = cPent | Me | b) 0.59 (petroleum ether ethyl acetate = 10:1) | | LXIII |
| LXXX | 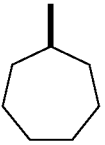 = cHex | Me | b) 0.62 (Petroleum ether ethyl acetate = 10:1) | | LXIII |
| LXXXI | cHex | tBu | b) 0.72 (I) | | LXV |
| LXXXII | 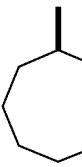 = cHept | Me | b) 0.57 (I) | | LXIII |
| LXXXIII | cHept | tBu | b) 0.67 (I) | | LXV |
| LXXXIV | 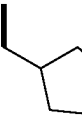 = cOct | tBu | b) 0.77 (I) | | LXV |
| LXXXV | 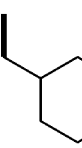 | tBu | (H) | | LXV |
| LXXXVI |  | tBu | b) 0.82 (Q) | | LXV |

TABLE IV

The compounds of Table IV are prepared analogously to the procedure of Example LXVI; only 2.5 equivalents of the base and 2.5 equivalents of the halogenoalkane (in the case of the cyclic alkyl radicals 1.2 equivalents of the α,ω-dihalogenoalkane) are employed.

| Ex. No. | X | Y | a) M.p.(° C.)<br>b) $R_f$ (Solvent) | Spektra | Starting material from Ex. No. |
|---|---|---|---|---|---|
| LXXXVII | C(CH₃)₂ | tBu | b) 0.68 (F) | | LXV |
| LXXXVIII | C(CH₂CH₃)₂ | tBu | b) 0.32 (Petroleum ether) | | LXV |
| LXXXIX | C(CH₂CH₂CH₃)₂ | tBu | b) 0.84 (B) | | LXV |
| XC | C(CH₂CH₂CH₂CH₃)₂ | tBu | b) 0.82 (C) | | LXV |
| XCI | cyclopentyl | tBu | b) 0.23 (petroleum ether) | | LXV |
| XCII | cyclohexyl | tBu | b) 0.21 (petroleum ether) | | LXV |
| XCIII | cycloheptyl | tBu | b) 0.26 (petroleum ether) | | LXV |

EXAMPLE XCIV tert-Butyl 2-(4-bromomethyl-phenyl)-2-cyclopentyl-acetate

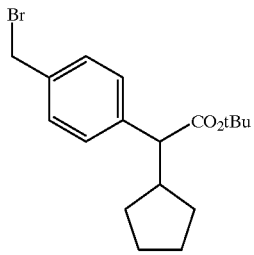

27.4 g (0.1 mol) of the compound from Example LXV are dissolved in 200 ml of carbon tetrachloride and the solution is heated to boiling. After addition of 0.82 g of azobisisobutyronitrile, 18.7 g (0.105 mol) of N-bromosuccinimide are added in portions and the mixture is then refluxed for 1 h, cooled to 0° C. and the succinimide is filtered off. After concentrating the filtrate the product precipitates. It is washed with petroleum ether (40/60) and dried.

Yield: 20 g (57%)

Melting point: 73–76° C.

The compounds of Table V are prepared analogously to the procedure of Example No. XCIV.

TABLE V

[Structure: 4-(bromomethyl)phenyl-CH(X)-C(=O)-O-Y]

| Ex. No. | —X | —Y | a) M.p.(° C.)<br>b) R$_f$ (Solvent) | Spektra | Starting material from Ex. No. |
|---|---|---|---|---|---|
| XCV | —H | Me | b) 0.45 (XA) | | LXIII |
| XCVI | —H | tBu | b) 0.54 (V) | | LXV |
| XCVII | Me | tBu | b) 0.78 (I) | | LXVII |
| XCVIII | Et | tBu | b) 0.75 (I) | | LXVIII |
| XCIX | nPr | tBu | b) 0.80 (I) | | LXIX |
| C | iPr | Me | b) 0.78 (M) | | LXX |
| CI | iPr | tBu | b) 0.90 (Q) | | LXXI |
| CII | nBu | tBu | b) 0.82 (I) | | LXXII |
| CIII | iBu | tBu | b) 0.86 (M) | | LXXIII |
| CIV | nPent | tBu | b) 0.73 (H) | | LXXIV |
| CV | iPent | tBu | | MS: 372, 374<br>(([M + NH$_4$]$^+$; 79%, 77%) | LXXV |
| CVI | —CH(CH$_2$CH$_3$)$_2$ | tBu | | MS: 372, 372<br>([M + NH$_4$]$^+$; 4%, 4%) | LXXVI |
| CVII | nHex | tBu | b) 0.85 (I) | | LXXVII |
| CVIII | —CH$_2$CH(CH$_2$CH$_3$)$_2$ | tBu | | MS: 386, 388<br>([M + NH$_4$]$^+$; 14%, 14%) | LXXVIII |
| CIX | cPent | Me | b) 0.63 (petroleum ether ethyl acetate = 10:1) | | LXXIX |
| CX | cHex | Me | b) 0.47 (petroleum ether ethyl acetate = 20:1) | | LXXX |
| CXI | cHex | tBu | b) 0.58 (petroleum ether ethyl acetate = 10:1) | | LXXXI |
| CXII | cHept | Me | b) 0.59 (I) | | LXXXII |
| CXIII | cHept | tBu | b) 0.84 (M) | | LXXXIII |
| CXIV | cOct | tBu | b) 0.49 (petroleum ether ethyl acetate = 10:1) | | LXXXIV |
| CXV | —CH$_2$-cPent | tBu | b) 0.58 (A) | | LXXXV |
| CXVI | —CH$_2$-cHex | tBu | $^1$H-NMR (250 MHz, CDCl$_3$, TMS):<br>δ = 3.58(M; 1H), 4.49 (s, 2H) ppm | | LXXXVI |

TABLE VI

[Structure: 4-(bromomethyl)phenyl-X-C(=O)-O-Y]

| Ex. No. | X | —Y | a) M.p.(° C.)<br>b) $R_f$ (Solvent) | Spektra | Starting material from Ex. No. |
|---|---|---|---|---|---|
| CXVII | C(CH₃)₂ (H₃C, CH₃) | tBu | b) 0.68 (F) | | LXXXVII |
| CXVIII | C(CH₂CH₃)₂ (H₃CH₂C, CH₂CH₃) | tBu | b) 0.38 (petroleum ether ethyl acetate = 20:1) | | LXXXVIII |
| CXIX | C(CH₂CH₂CH₃)₂ (H₃C(H₂C)₂, (CH₂)₂CH₃) | tBu | b) 0.84 (B) | | LXXXIX |
| CXX | C(CH₂CH₂CH₂CH₃)₂ (H₃C(H₂C)₃, (CH₂)₃CH₃) | tBu | b) 0.82 (C) | | XC |
| CXXI | cyclopentyl (1,1-disubstituted) | tBu | | MS: 356, 358<br>([M + NH₄]⁺; 9%, 11%) | XCI |
| CXXII | cyclohexyl (1,1-disubstituted) | tBu | | MS: 370, 372<br>([M + NH₄]⁺; 5%, 5%) | XCII |
| CXXIII | cycloheptyl (1,1-disubstituted) | tBu | b) 0.47 (petroleum ether ethyl acetate = 20:1) | | XCIII |

EXAMPLE CXXIV

L-Menthyl 2(S)-2-cyclopentyl-2[4-(2,4-dimethyl-α-carbolin-9-yl)methyl]-phenyl-acetate

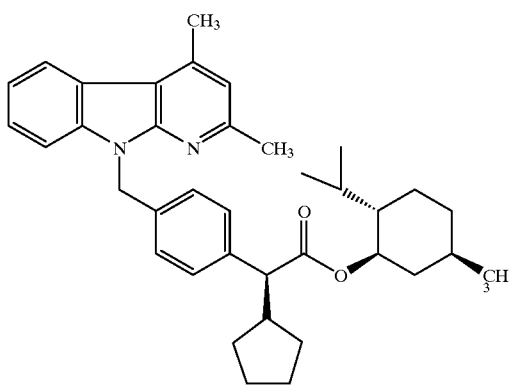

The reaction is carried out under a nitrogen atmosphere. 480 g (2.44 mol) of carboline are suspended in 4.13 l of dimethylformamide and treated with reaction with 287.7 g of potassium tert-butoxide dissolved in 1 l of dimethylformamide. The reaction solution warms to 30° C. After 30 min, the mixture is cooled to 20° C. 1.707 kg (2.69 mol) of 69% strength menthyl ester bromide (CXXXV), dissolved in 1.56 l of dimethylformamide, are then added dropwise such that the internal temperature does not rise above 35° C. After a reaction time of a further 15 min, the reaction solution is poured into a mixture of 1.8 l of 10% strength sodium chloride solution and 13 l of ethyl acetate. After stirring for 20 min, the ethyl acetate phase is separated off and extracted twice with 3 l of 10% strength sodium chloride solution each time. After drying the organic phase over sodium sulphate, ethyl acetate is distilled off in vacuo at about 40° C. The syrupy residue is taken up in 4.4 l of methanol and stirred under reflux for 30 min and at room temperature for 12 h. The precipitated crystals are filtered off with suction, washed with methanol and dried in vacuo at 400° C.

Yield: 947 g (70.6% of theory)

Melting point: 142° C.

EXAMPLE CXXV 2-(S)-2-Cyclopentyl-2-[4-(2,4-dimethyl-α-carbolin-9-yl)-methyl]phenylacetic acid

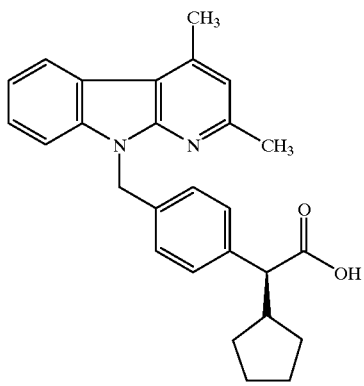

947 g (1.72 mol) of the compound from Example CXXIV are treated with 2.4 l of formic acid. 1.21 l of aqueous hydrobromic acid (48% strength) are added dropwise with stirring The suspension obtained is stirred at 95–98° C. for 6 hours and then cooled to room temperature. The reaction solution is treated with stirring with 1.6 l of isopropanol and 3.2 l of water. A pH of 5 is established with slight cooling using 45% strength sodium hydroxide solution (consumption of sodium hydroxide solution: 5.2 kg). The precipitate is filtered off with suction, washed twice with 5.7 l of water and sucked dry. The water-moist product is then extracted by stirring at room temperature for 2 hours in 2.6 l of isopropanol. The crystallizate is filtered off with suction, washed with 2.8 l of isopropanol and dried in vacuo at 60° C.

Yield: 574 g (81% of theory)

Melting point: 197–199° C.

EXAMPLE CXXVI 2-(S)-2-Cyclopentyl-2-[4-(2,4-dimethyl-α-carbolin-9-yl)-methyl]phenylacetyl chloride

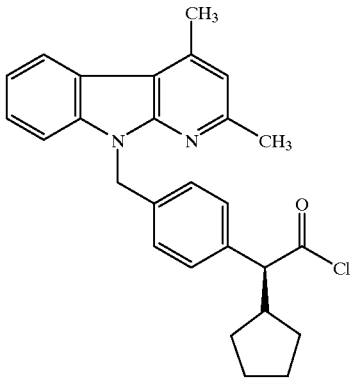

A suspension of 350 g (0.85 mol) of the compound from Example CXXV in 3 l of methylene chloride is heated to reflux with stirring. In the course of 1 h, 95 ml (155 g, 1.3 mol) of thionyl chloride are added dropwise and the mixture is stirred at reflux temperature for a further 2 h. The reaction solution is then cooled to room temperature, concentrated in vacuo at 25–30° C. until crystallization begins and treated with 2.5 l of toluene. A further 2.3 l of solvent are distilled off in vacuo at a temperature of 30–40° C. After cooling to about 20° C., 1.2 l of toluene are added to the mixture. The suspension is cooled to 0–50° C., stirred at this temperature for 1 h and filtered off with suction, and the solid is washed with 1.4 l of toluene and sucked dry. The toluene-moist product is reacted without further characterization.

EXAMPLE CXXVII

Methyl 2-cyclopentyl-2-(3-tolyl)-acetate

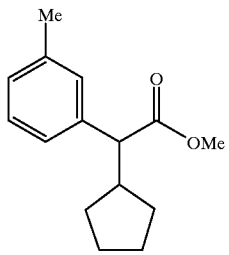

The title compound is prepared from methyl 2-(3-tolyl)-acetate analogously to the procedure of Example LXIII.

$R_f$=0.56 (P)

EXAMPLE CXXVIII

Methyl 2-(3-bromomethyl-phenyl)-2-cyclopentyl-acetate

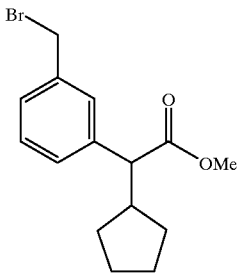

The title compound is prepared from the compound of Example CXXVII analogously to the procedure for Example XCIV.

$R_f$=0.40 (P)

EXAMPLE CXXIX

2(R/S)-2-Cyclopentyl-2-(4-methylpheny)-acetic acid

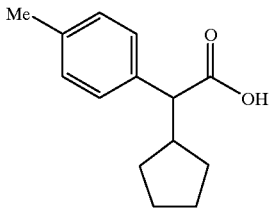

2.0 kg (7.2 mol) of the compound from Example LXV are dissolved in 4 l of dioxane in a 40 l stirring vessel with an attached scrubber. After addition of 4.5 l of concentrated hydrochloric acid, the mixture is stirred at 50° C. until conversion is complete (3 h). The reaction mixture is treated with ice and adjusted to pH=12 with concentrated sodium hydroxide solution. After addition of water until the solids are completely dissolved, the mixture is washed with acetic acid, the organic phase is washed with dilute sodium hydroxide solution and the combined aqueous phases are adjusted to pH=1 with concentrated hydrochloric acid with cooling. The mixture is washed twice with ethyl acetate, dried over sodium sulphate and concentrated.

Yield: 1.27 kg, 81% of theory

Melting point: 92° C.

$R_f$=0.20 (petroleum ether:ethyl acetate=4:1)

$^1$H-NMR (CDCl$_3$, 200 MHz, TMS): δ=0.98 (m, 1H); 1.20–1.71 (m, 6H); 1.82–2.05 (m, 1H); 2.31 (s, 3H); 2.52 (m, 1H); 3.21 (d, 1H); 7.10 (m, 2H); 7.21 (m, 2H); 11.90 (br, s, 1H) ppm.

EXAMPLE CXXX (S)-(+)-2-Cyclopentyl-2-(4-methylphenyl)-acetic acid

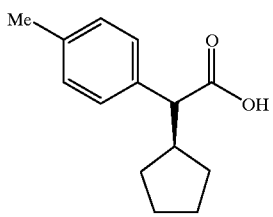

2.4 l of THF and 129.7 g (1.28 mol) of triethylamine are added with stirring to a suspension of 560 g (2.57 mol) of the compound from Example CXXIX in 4.8 l of water. The resulting solution is warmed to 60° C., 155.4 g (1.28 mmol) of (S)-(−)-phenethylamine are added and the suspension obtained is stirred at 60° C. for 2 h. The reaction mixture is cooled to 20° C., and the precipitate is filtered off with suction, washed with 2.4 l of water/THF (2:1) and dried in vacuo.

Yield: 360 g of phenethylammonium salt; 41.3% of theory based on racemate Ex. No. CXXIX 745 g (2.2 mol) of phenethylammonium salt are suspended in 3 l of water, acidified (pH=1) with dilute hydrochloric acid (1:1) and stirred for 30 minutes. The oily suspension is washed three times with 1 l of dichloromethane each time, and the combined organic phases are washed with water, dried over sodium sulphate and concentrated, whereupon the residue crystallizes.

Yield: 475 g, 37.3% of theory based on racemate Ex. No. CXXIX ee: 96.3% (HPLC)

Melting point: 66° C.

By crystallization of the phenethylammonium salt from THF and liberation of Example No. CXXX, the pure enantiomer is obtained as described above: ee: >99.5% (HPLC)

Specific rotation: $[α]_D^{20}$=+59.55 (ethanol/c=0.85)

The HPLC method for the determination of the ee value is as follows (the racemic compound from Example CXXIX serves as a comparison):

| Column: | Chiracel OJ (Daicel) |
|---|---|
| Particle size: | 10μ |
| Packing: | 250 × 2 mm (Grom) |
| Mobile phase: | n-heptane: 2-propanol = 97:3 |
| Flow rate: | 0.2 ml/min |
| Inlet pressure: | 22 bar |

EXAMPLE CXXXI tert-Butyl (S)-(+)-2-cyclopentyl-2-(4-methylphenyl) acetate

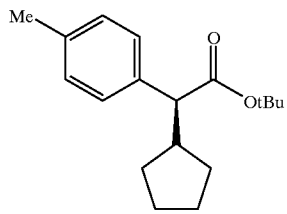

6 ml of concentrated sulphuric acid are added to a solution of 465 g (2.13 mol) of the compound from Example CXXX in 1.4 l of dichloromethane, a temperature of about 10° C. being established. 550 ml (5 mol) of isobutene are condensed into a Dewar vessel and added to the starting material solution in one portion. The reaction mixture is stirred overnight. To complete the conversion, a further 6 ml of concentrated sulphuric acid and 500 ml of isobutene are added and the mixture is stirred overnight. After addition of 40 g of potassium carbonate, the mixture is stirred for 3 h and 2 l of water are added to it, a vigorous evolution of gas initially occurring. The mixture is washed three times using 2 l of dichloromethane each time, and the combined organic phases are washed with 5 l of sodium chloride solution, dried over sodium sulphate and concentrated to give an oil, which slowly crystallizes.

Yield: 480 g, 82% of theory

Melting point: 45° C.

$R_f$=0.90 (toluene:ethyl acetate=8:2)

EXAMPLE CXXXII tert-Butyl (S)-(+)-2-(4-bromomethylphenyl)-2-cyclopentyl-acetate

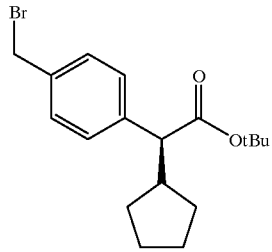

480 g (1.75 mol) of the compound from Example CXXXI are dissolved in 3.4 l of tetrachloromethane under reflux in a 10 l flask and the mixture is treated with 70 g of a total amount of 311 g (1.75 mol) of NBS and 14 g (0.085 mol) of AIBN. The reaction commences after refluxing for about 1 h; after it subsides further NBS is added in 50 g portions. After refluxing for 5 h and subsequently standing at room temperature overnight, for working up the mixture is cooled to 0° C., and the succinimide is filtered off with suction and washed with 600 ml of tetrachloromethane. The combined filtrates are concentrated and residual solvent is removed in vacuo to constant weight.

Crude yield: 570 g, about 100% of theory

HPLC: 68.8% (15.5% starting material, 10.1% dibromo compound)

The pure substance is obtained by column chromatography $R_f$=0.42 (Q)

$^1$H-NMR (CDCl$_3$, 200 MHz, TMS): δ=0.98 (m, 1H); 1.22–1.71 (m, 6H); 1.40 (s, 9H); 1.90 (m, 1H); 2.47 (m, 1H); 3.16 (d, 1H); 4.49 (s, 2H); 7.32 (m, 4H) ppm.

EXAMPLE CXXXIII (L)-Menthyl 2-(4-tolyl)-acetate

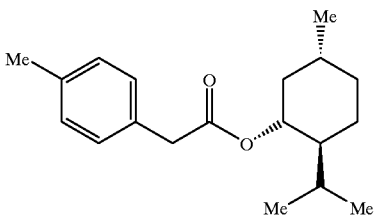

3.15 kg of p-tolylacetic acid and 9.45 l of toluene are initially introduced. 3.115 kg of L-menthol and 21.4 ml of methanesulphonic acid are added with stirring and cooling. The mixture is then heated to reflux temperature and the corresponding amount of water is removed by means of a water separator in the course of 16 to 20 hours. After cooling to room temperature, the mixture is extracted once by stirring with 4.41 l of saturated sodium hydrogen carbonate solution and twice with 4.41 l of water each time. The organic phase is freed from the solvent and affords 5.725 kg of desired compound (GC 99.9%, retention time 19.49 min).

$^1$H-NMR (CDCl$_3$, ppm): 7.05–7.15 (4H, m); 4.55 (1H, txd); 3.5 (2H, s); 2.8 (3H, s); 0.65 (3H, s).

EXAMPLE CXXXIV (L)-Menthyl 2-(S)-2-cyclopentyl-2-(4-tolyl)-acetate

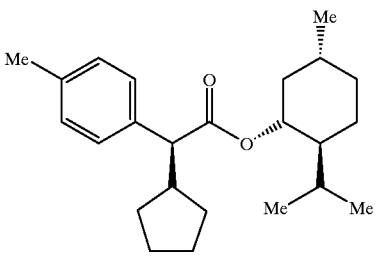

1.575 kg of potassium tert-butoxide are dissolved in 3.75 l of DMF at room temperature. The mixture is cooled to 10° C. and 2.678 kg of the compound from Example CXXXIII are allowed to run in at this temperature in the course of 45 minutes and are rinsed in with 0.375 l of DMF. 1.658 kg of cyclopentyl bromide are then pumped in in the course of 1 to 2 hours with full cooling. The suspension is stirred for a further hour without cooling and then cooled to −70° C. On reaching −10° C., the mixture is seeded with the correct diastereomer and then further cooled to −70° C. After reaching −70° C., the mixture is stirred at this temperature for 3 to 4 hours. Working up is carried out by introducing the reaction suspension into a mixture of 1.5 kg of ice and 6 kg of water. The mixture is then stirred overnight at 0 to 2° C. Working up is carried out by filtering off the suspension with suction and washing the crystals with a total of 2.5 l of water.

The crystals are dried at 45° C. in a vacuum drying oven. 3.289 kg of an 85 to 15 diastereomer mixture are obtained. 4.345 kg of a mixture prepared as described above are dissolved in 21.75 l of DMF at 30 to 35° C. After seeding with the correct diastereomer and cooling to room temperature, the mixture is stirred overnight and cooled to 0 to 5° C. the next morning. After 1 to 2 hours at this temperature, the crystals are filtered off with suction and dried or recrystallized again. By repeating the methanol crystallization one or two times, material having a diastereomer purity of ≧99.5% can be prepared (GC retention time 22.61 min).

The yield of diastereomerically pure title compound over the stages cyclopentylation and crystallization in pure form is 65–70% and can be raised to 75–80% by recrystallization or by epimerization of the mother liquors with potassium tert-butoxide in DMF and crystallization of the crude diastereomer mixture again.

$^{13}$C-NMR (CDCl$_3$, CH signals, ppm) 128.90; 128.92; 73.96; 57.85; 46.92; 43.13; 31.28; 25.96.

EXAMPLE CXXXV (L)-Menthyl 2-(S)-2-(4-bromomethyl-phenyl)-2-cyclopentyl-acetate

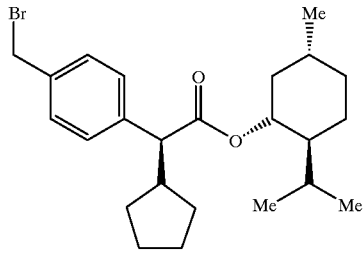

1.40 kg of the compound from Example CXXXIV are warmed to 80° C. in 13.74 l of chlorobenzene. 0.618 kg of 1,3-dibromo-5,5-dimethylhydantoin is then added and the mixture is warmed further to 85° C. At this temperature, 20.4 g of AIBN are then added to start the reaction. The temperature rises after the start of the reaction to 90 to 105° C., but then falls again to approximately 85° C. Reaction is carried out for a total of 2 hours. The vessel contents are then cooled to room temperature and the mixture is stirred for one hour. The precipitated crystals are filtered off with suction and the filtrate is freed from the solvent. The residual oil is 61.2% strength according to HPLC analysis (retention time 14.68 min.). 1.69 kg are obtained. The mixture can be employed in crude form in the following alkylations. Chromatography and subsequent crystallization yield a white powder of melting point 57–58° C., with the correct CH analysis.

$^1$H-NMR (CDCl$_3$, ppm): 7.3 (4H, s); 4.65 (1H, txd); 4.45 (2H, s); 3.35 (1H, d); 0.65 (3H, d).

EXAMPLE CXXXVI

Methyl 2-(R/S)-2-phenyl-2-(4-methyl)phenylacetate

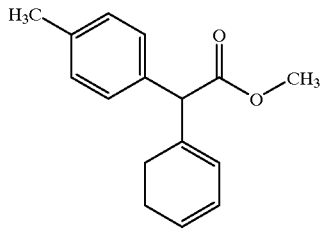

21.0 g (100 mmol) of 2-phenyl-1-(4-methyl)phenyl-1-oxoethane and 38.8 g (120 mmol) of iodobenzene diacetate are dissolved in 300 ml of trimethyl orthoformate. 19.6 g of concentrated sulphuric acid are added to this solution, and the solution is stirred at 60° C. for 6 h. The solution is cooled to room temperature, diluted with water and extracted with diethyl ether. The combined organic phases are dried over sodium sulphate and concentrated in a rotary evaporator. The residue is purified by column chromatography.

Yield: 13.1 g(55%)

$R_f$=0.33 (Q)

MS (FAB): 241 (25%), 181 (100%).

$^1$H-NMR (200 MHz, CDCl$_3$, TMS): δ=7.3–7.10 (m, 9H); 4.99 (s, 1H); 3.73 (s, 3H); 2.31 (s, 3H) ppm.

EXAMPLE CXXXVII

Methyl 2-(R/S)-2-(4-chlorophenyl)-2-(4-tolyl)-acetate

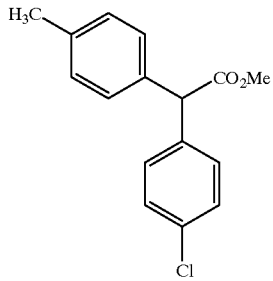

The title compound is prepared in analogy to the procedure of Example CXXXVI.

PREPARATION EXAMPLES

Example 1

2-(S)-2-Cyclopentyl-2-[4-(2,4-dimethyl-α-carbolin-9-yl)-methyl]phenylacetic acid N-propylamide

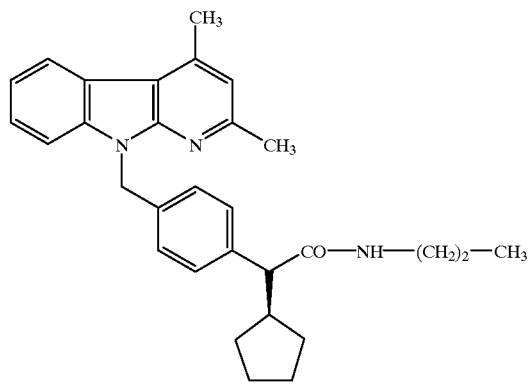

200 mg (0.46 mmol) of tolylacetyl chloride (CXXVI) are dissolved in 2 ml of methylene chloride, 28 mg (0.46 mmol) of propylamine and 0.1 ml (0.70 mmol) of triethylamine are added and the mixture is stirred at room temperature for 45 min. It is then treated with 1 ml of water, stirred at room temperature for 5 min and added to a glass ready-to-use column (Extrelut3, E. Merck). After 5 min, the column is eluted with 15 ml of methylene chloride, and the filtrate is concentrated and dried in vacuo.

Yield: 177 mg (85% of theory)

$R_f$=0.74 (A)

The compounds listed in Table 1 are prepared in analogy to the procedure of Example 1:

TABLE 1

| Ex. No. | $R^5$ | $R^6$ | Yield (% of theory) | $R_f$/M.p. (° C.) |
|---|---|---|---|---|
| 2 | Ph | H | 90 | 0.85 (A) |
| 3 | —CH$_2$—CH$_2$OCH$_2$CH$_2$— | | 96 | 0.70 (A) |
| 4 | cyclopentylmethyl | H | 89 | 0.75 (A) |
| 5 | isobutyl | H | 79 | 0.70 (A) |
| 6 | —(CH$_2$)$_7$— | | 91 | 0.84 (A) |
| 7 | Me | H | 90 | 0.73 (A) |
| 8 | Et | H | 69 | 201° C. |
| 9 | —(CH$_2$)$_3$—Ph | H | 89 | 118° C. |
| 10 | n-Oct | n-Oct | 92 | 0.95 (A) |
| 11 | isopropyl | H | 35 | 235° C. |
| 12 | n-Hex | n-Hex | 53 | 0.93 (A) |
| 13 | (S)-CH(CH$_3$)CH$_2$OH | H | 64 | 234° C. |
| 14 | (R)-CH(CH$_3$)CH$_2$OH | H | 69 | 232° C. |
| 15 | (S)-CH(CH$_3$)Napht | H | 79 | 240° C. |
| 16 | (R)-CH(CH$_3$)Napht | H | 73 | 248° C. |
| 17 | —CH$_2$CF$_3$ | H | 62 | 216° C. |
| 18 | (S)-CH(iPr)CH$_2$OH | H | 82 | 185° C. |
| 19 | —CH$_2$CH$_2$OH | H | 61 | 198° C. |
| 20 | n-Pent | H | 88 | 178° C. |
| 21 | n-Hex | H | 88 | 178° C. |
| 22 | n-Oct | H | 90 | 0.89 (A) |
| 23 | n-Pr | H | 84 | 0.74 (A) |

TABLE 1-continued

| Ex. No. | R⁵ | R⁶ | Yield (% of theory) | $R_f$/M.p. (° C.) |
|---|---|---|---|---|
| 24 | (ethyl-substituted bicyclic isoindoline with N-CH₂Ph) | H | 24 | 0.58 (W) |
| 25 | (ethyl-substituted bicyclic isoindoline with N-CH₂CH₂Ph) | H | 40 | 0.52 (W) |
| 26 | HOCH₂-C(CH₃)(CH₂Ph)- | H | 35 | 0.74 (W) |
| 27 | (diethyl norbornene with OCH₃) | | 37 | 0.80 (W) |

Example 28

2-(S)-2-Cyclopentyl-2-[4-(2,4-dimethyl-α-carbolin-9-yl)-methylphenyl]acetic acid N-(1-phenyl-ethen-1-yl)amide

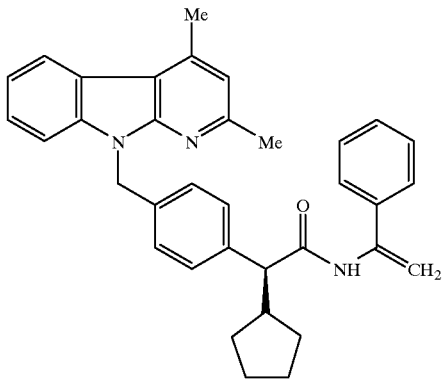

2.00 g (3.76 mmol) of 2-(S)-2-cyclopentyl-2-[4-(2,4-dimethyl-α-carbolin-9-yl)methylphenyl]-acetic acid N-((1R)-1-phenyl-2-hydroxy)-ethanamide are dissolved in 20 ml of anhydrous DMF, and the solution is treated with 0.52 ml (3.76 mmol) of triethylamine and stirred with mesyl chloride at −30° C. After 2 hours, the mixture is warmed to 20° C., treated with a further 1.04 ml (7.52 mmol) of triethylamine and stirred for 20 hours. The reaction mixture is diluted with diethyl ether and an aqueous buffer of pH=2 (Merck), the phases are separated and the organic phase is evaporated in vacuo. The residue is recrystallized in methanol, and the crystals are filtered off with suction after cooling washed with cold methanol and dried in vacuo over phosphorus pentoxide.

Yield: 0.81 g (42% of theory)

$R_f$=0.60 (G)

¹H-NMR (d₆-DMSO, 200 MHz, TMS): δ=3.84 (dd, 1H); 4.53 (dd, 1H); 5.08 (dd, 1H) ppm.

MS (ES): m/z=514 ([M+H]⁺, 100%).

Example 29

2-(S)-2-cyclohexyl-2-[4-{(2,4-dimethyl-α-carbolin-9-yl)-methyl}phenyl]acetic acid n-(1-phenyl-ethen-1-yl)amide

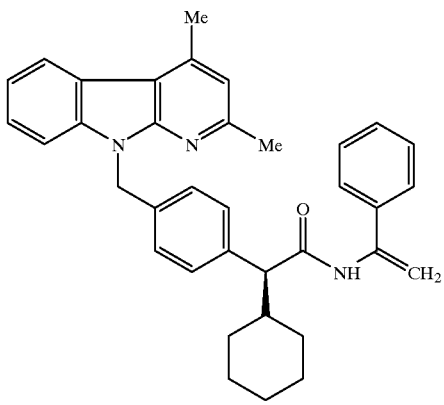

In analogy to the procedure of Example 24, the title compound is prepared from 2-(S)-2-cyclohexyl-2-[4-(2,4-dimethyl-α-carbolin-9-yl)-methylphenyl]-acetic acid N-((1R)-1-phenyl-2-hydroxy)-ethanamide $R_f$=0.63 (g)

MS (ES): m/z=528 ([M+H]$^+$, 100%).

What is claimed is:

1. An arylacetamide of the formula (I)

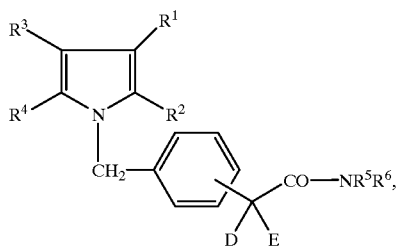

(I)

in which

R$^1$ and R$^2$, including the double bond connecting them, together form a pyridyl ring of the formula

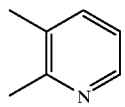

R$^3$ and R$^4$, including the double bond connecting them, together form a phenyl ring, where all ring systems mentioned under R$^1$/R$^2$ and R$^3$/R$^4$ are optionally substituted up to 3 times in an identical or different manner by halogen, trifluoromethyl, carboxyl, hydroxyl, by straight-chain or branched alkoxy or alkoxycarbonyl each having up to 6 carbon atoms or by straight-chain or branched alkyl having up to 6 carbon atoms, which for its part can be substituted by hydroxyl or by straight- chain or branched alkoxy having up to 4 carbon atoms, D and E are identical or different and represent hydrogen, cycloalkyl having 3 to 8 carbon atoms or straight-chain or branched alkyl having up to 10 carbon atoms, which is optionally substituted by cycloalkyl having 3 to 6 carbon atoms, or represent phenyl which is optionally substituted by halogen or trifluoromethyl, or D and E together; including the CH group, form a 4- to 8-membered carbocyclic system, R$^5$ represents hydrogen, straight-chain or branched alkyl having up to 12 carbon atoms or cycloalkyl having 3 to 8 carbon atoms, R$^6$ represents cycloalkyl having 3 to 8 carbon atoms or phenyl, or represents straight-chain or branched all having up to 9 carbon atoms, which is optionally substituted by hydroxyl, naphthyl or trifluoromethyl, or R$^6$ represents a radical of the formula —(CH$_2$)$_n$—R$^8$, in which n denotes a number 2, 3, 4 or 5, R$^8$ denotes naphthyl which is optionally substituted by carboxyl, trifluoromethyl, halogen, hydroxyl, trifluoromethoxy or by straight-chain or branched alkyl, acyl, alkoxy or alkoxycarbonyl each having up to 6 carbon atoms, or represents a radical of the formula

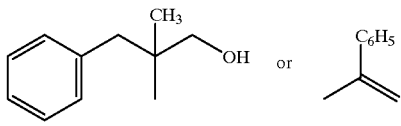

optionally in an isomeric form, or a salt thereof.

2. An arylacetamide of the formula according to claim 1 in which

R$^1$ and R$^2$, including the double bond connecting them, together form a pyridyl ring of the formula

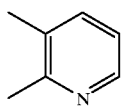

R$^3$ and R$^4$ including the double bond connecting them, together form a phenyl ring, where all ring systems mentioned under R$^1$/R$^2$ and R$^3$/R$^4$ are optionally substituted up to 2 times in an identical or different manner by fluorine, chlorine, bromine, trifluoromethyl, carboxyl, hydroxyl, by straight-chain or branched alkoxy or alkoxycarbonyl each having up to 4 carbon atoms or by straight-chain or branched alkyl having up to 4 carbon atoms, which for its part can be substituted by hydroxyl or by straight-chain or branched alkoxy having up to 3 carbon atoms, D and E are identical or different and represent hydrogen, cyclopropyl, cyclobutyl, cyclopentyl, cyclohexyl, cycloheptyl, cyclooctyl or straight-chain or branched alkyl having up to 8 carbon atoms, which is optionally substituted by cyclopropyl, cyclopentyl or cyclohexyl, or represent phenyl which is optionally substituted by fluorine, chlorine or bromine, or D and E together, including the CH group, form a cyclobutyl, cyclopentyl, cyclohexyl, cycloheptyl or cyclooctyl ring R$^5$ represents hydrogen, straight-chain or branched alkyl having up to 10 carbon atoms, cyclopropyl, cyclobutyl, cyclopentyl, cyclohexyl, cycloheptyl or cyclooctyl, R$^6$ represents cyclopropyl, cyclobutyl, cyclopentyl, cyclohexyl, cycloheptyl, cyclooctyl or phenyl, or represents straight-chain or branched alkyl having up to 7 carbon atoms, which is optionally substituted by hydroxyl, naphthyl, or trifluoromethyl, or R$^6$ represents a radical of the formula —(CH$_2$)$_n$—R$^8$, in which n denotes a number 2, 3 or 4, R$^8$ denotes naphthyl which is optionally substituted by trifluoromethyl, fluorine, chlorine, bromine, hydroxyl, trifluoromethoxy or by straight-chain or branched alkyl, alkoxy or alkoxycarbonyl each having up to 5 carbon atoms, or
represents a radical of the formula

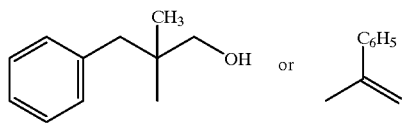

optionally in an isomeric form, or a salt thereof.

3. An arylacetimide of the formula according to claim 1 in which $R^1$ and $R^2$, including the double bond connecting them, together form a pyridyl ring of the formula

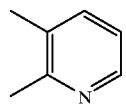

$R^3$ and $R^4$, including the double bond connecting them, together form a phenyl ring,
where all ring systems mentioned under $R^1/R^2$ and $R^3/R^4$ are optionally substituted up to 2 times in an identical or different manner by fluorine, chlorine, bromine, trifluoromethyl, carboxyl, hydroxyl, by straight-chain or branched alkoxy or alkoxycarbonyl each having up to 3 carbon atoms or by straight-chain or branched alkyl having up to 3 carbon atoms, which for its part can be substituted by hydroxyl, methoxy or ethoxy, D and E are identical or different and represent hydrogen, cyclopropyl, cyclobutyl, cyclopentyl, cyclohexyl, cyclaheptyl, cyclooctyl or straight-chain or branched alkyl having up to 6 carbon atoms, which is optionally substituted by cyclopentyl or cyclohexyl, or represent phenyl which is optionally substituted by fluorine, chlorine or bromine,
or
D and E together, including the CH group, form a cyclopentyl cyclohexyl or cycloheptyl ring, $R^5$ represents hydrogen, straight-chain or branched alkyl having up to 8 carbon atoms, cyclopentyl, cyclobexyl or cycloheptyl, $R^6$ represents cyclopentyl, cyclooctyl or pbenyl, or represents straight-chain or branched alkyl having up to 6 carbon atoms, which is optionally substituted by hydroxyl, naphthyl, trifluoromethyl, $R^6$ represents a radical of the formula $-(CH_2)_n-R^8$, in which n denotes a number 2 or 3, $R^8$ denotes naphthyl which is optionally substituted by trifluoromethyl, fluorine, chlorine, hydroxyl, trifluoromethoxy or by straight-chain or branched alkyl, alkoxy or alkoxycarbonyl each having up to 3 carbon atoms, or
represents a radical of the formula

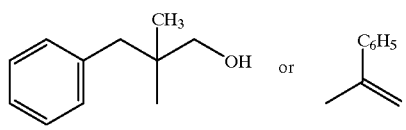

optionally in an isomeric form, or a salt thereof.

4. A pharmaceutical composition comprising a compound according to claim 1 and a pharmaceutically acceptable carrier.

5. A method for the treatment of arteriosclerosis, said method comprising administering to a patient in need thereof an effective amount therefor of a compound according to claim 1.

6. A method for the reduction of the formation and/or the release of ApoB-100-associated lipoprotein, said method comprising administering to a patient in need thereof an effective amount therefor of a compound according to claim 1.

* * * * *

UNITED STATES PATENT AND TRADEMARK OFFICE
CERTIFICATE OF CORRECTION

PATENT NO. : 6,194,424 B1
DATED : February 27, 2001
INVENTOR(S) : Peter Eckenberg et al.

It is certified that error appears in the above-identified patent and that said Letters Patent is hereby corrected as shown below:

Column 66,
Line 8, after "trifluoromethyl" insert -- or --

Signed and Sealed this

First Day of June, 2004

JON W. DUDAS
*Acting Director of the United States Patent and Trademark Office*